(12) United States Patent
Smith et al.

(10) Patent No.: US 6,993,818 B2
(45) Date of Patent: Feb. 7, 2006

(54) MULTI-FIXTURE ASSEMBLY OF CUTTING TOOLS

(75) Inventors: Norman Frank Smith, Albuquerque, NM (US); Samuel Lee Miller, Albuquerque, NM (US); Murray Steven Rodgers, Albuquerque, NM (US)

(73) Assignee: MEMX, Inc., Albuquerque, NM (US)

( * ) Notice: Subject to any disclaimer, the term of this patent is extended or adjusted under 35 U.S.C. 154(b) by 0 days.

(21) Appl. No.: 10/390,488

(22) Filed: Mar. 17, 2003

(65) Prior Publication Data

US 2004/0181927 A1   Sep. 23, 2004

(51) Int. Cl.
*B23P 25/00* (2006.01)

(52) U.S. Cl. .............. 29/458; 29/464; 29/469; 29/557; 29/558; 216/33; 438/460

(58) Field of Classification Search ........... 29/458, 29/464, 467, 469, 557, 558, 426.1; 216/2, 216/33; 438/460
See application file for complete search history.

(56) References Cited

U.S. PATENT DOCUMENTS

| | | | |
|---|---|---|---|
| 3,834,265 A | 9/1974 | Tafapolsky et al. ........... 83/651 |
| 3,894,337 A | 7/1975 | Jones ...................... 30/346.54 |
| 4,091,813 A | 5/1978 | Shaw et al. ............. 128/303.14 |
| 4,409,659 A | 10/1983 | Devine ....................... 364/475 |
| 4,534,827 A | 8/1985 | Henderson .................. 156/647 |
| 4,566,465 A | 1/1986 | Arhan et al. ................ 128/778 |
| 4,697,489 A | 10/1987 | Kim ............................. 83/856 |
| 5,201,987 A * | 4/1993 | Hawkins et al. ............... 216/2 |
| 5,317,938 A | 6/1994 | Juan et al. ................. 76/104.1 |
| 5,380,320 A | 1/1995 | Morris ........................ 606/33 |
| 5,527,744 A * | 6/1996 | Mignardi et al. .............. 216/2 |
| 5,579,583 A | 12/1996 | Mehregany et al. .......... 30/342 |
| 5,619,889 A | 4/1997 | Jones et al. ................ 76/104.1 |
| 5,683,592 A | 11/1997 | Bartholomew et al. ....... 216/24 |
| 5,700,382 A * | 12/1997 | Splett .......................... 216/24 |
| 5,842,387 A | 12/1998 | Marcus et al. ............. 76/104.1 |
| 5,882,532 A * | 3/1999 | Field et al. .................... 216/2 |

(Continued)

FOREIGN PATENT DOCUMENTS

JP      WO 02/098619 A1   12/2002   ................... 21/58

OTHER PUBLICATIONS

Trade Show Handout CD (Orlando, Florida, Oct. 18, 2002); Med-Logics, Inc.; "Calibrated Lasik Blades".

Primary Examiner—Essama Omgba
(74) Attorney, Agent, or Firm—Marsh Fischmann & Breyfogle LLP

(57) ABSTRACT

Multiple cutting blades (56) are fabricated from a wafer (130). This wafer (130) is disposed on a blade handle mounting fixture (224) such that a blade handle (24) maybe mounted on each of the individual blades (56). A cutting edge (80) of each blade (56) is maintained in spaced relation to the fixture (224) as these blade handles (24) are being mounted. Thereafter, the wafer (130) is transferred to a blade separation fixture (300). Each blade 56 is suspended above the fixture (300). An appropriate force is transmitted to the individual blades (56) to separate the same from the wafer (130). Separation preferably occurs before the blade (56) contacts the fixture (300). Thereafter, the blade (56) in effect pivots into an inclined position where its cutting edge (80) projects at least generally upwardly. Preferably, at no time does the cutting edge (80) of any blade (56) contact either the blade handle mounting fixture (224) or the blade separation fixture (300).

72 Claims, 25 Drawing Sheets

U.S. PATENT DOCUMENTS

| | | | |
|---|---|---|---|
| 5,928,161 A * | 7/1999 | Krulevitch et al. | 600/564 |
| 5,980,518 A | 11/1999 | Carr et al. | 606/45 |
| 5,985,217 A | 11/1999 | Krulevitch et al. | 422/99 |
| 6,121,118 A * | 9/2000 | Jin et al. | 438/460 |
| 6,132,446 A | 10/2000 | Hellenkamp et al. | 606/166 |
| 6,344,402 B1 * | 2/2002 | Sekiya | 438/460 |
| 6,353,204 B1 | 3/2002 | Spaay et al. | 219/121.72 |
| 6,387,778 B1 * | 5/2002 | Bonin et al. | 438/462 |
| 6,406,934 B1 * | 6/2002 | Glenn et al. | 438/106 |
| 6,544,590 B1 * | 4/2003 | Kodera et al. | 427/350 |
| 6,554,847 B2 * | 4/2003 | Cull | 606/166 |
| 6,615,496 B1 | 9/2003 | Fleming et al. | 30/350 |
| 6,623,498 B1 * | 9/2003 | Ziemer | 606/166 |
| 2002/0143351 A1 * | 10/2002 | Wortrich | 606/166 |
| 2004/0181246 A1 * | 9/2004 | Heppler | 606/167 |
| 2004/0181928 A1 * | 9/2004 | Smith et al. | 29/464 |
| 2005/0115047 A1 * | 6/2005 | Kley | 29/467 |

* cited by examiner

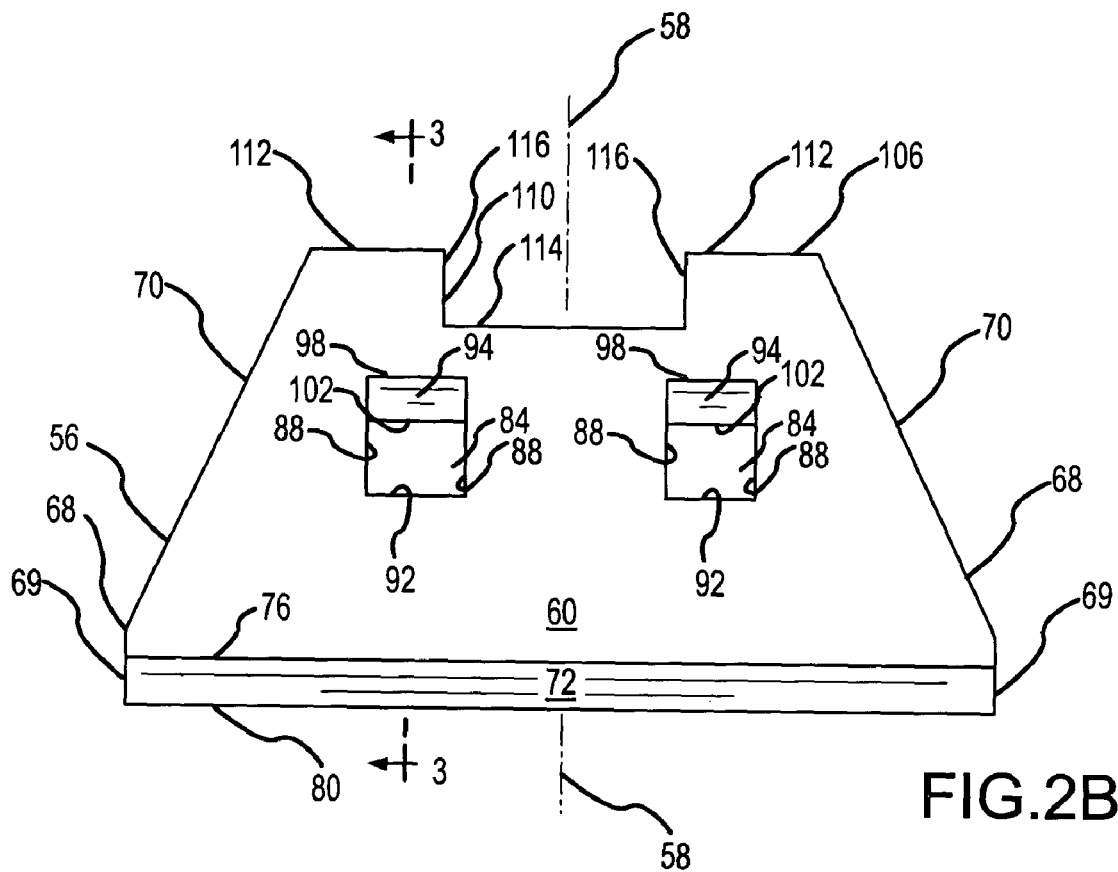
FIG.2B
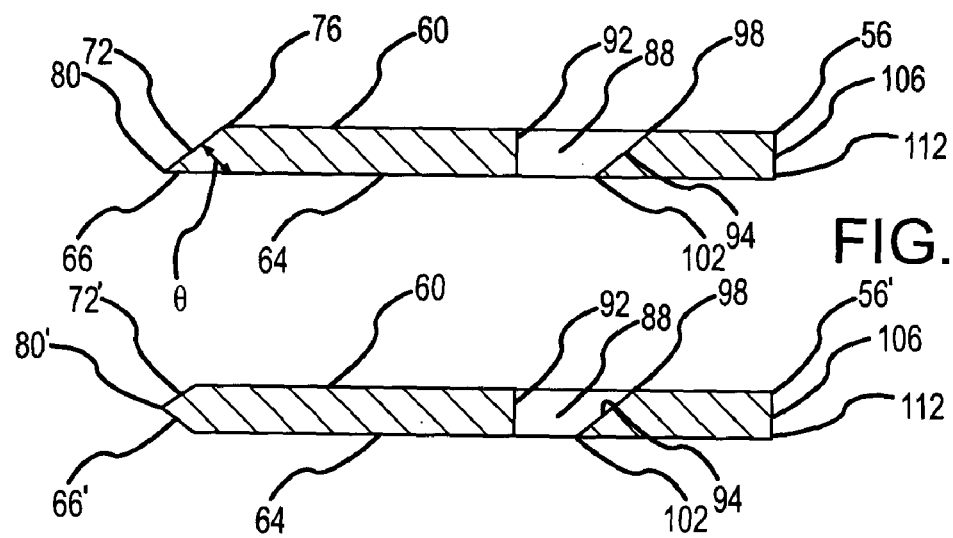
FIG.3A
FIG.3B

MULTI-FIXTURE ASSEMBLY OF CUTTING TOOLS

FIELD OF THE INVENTION

The present invention generally relates to assembling cutting tools having a separately formed blade handle and cutting blade and, more particularly, to using one fixture to mount the blade handle onto the cutting blade and another fixture to separate the cutting blade from a wafer on which the cutting blade is fabricated.

BACKGROUND OF THE INVENTION

Many types of blades exist for many types of applications. Blades are used for cutting biological materials of various types and for various applications. One application that is becoming quite prevalent is the cutting of human eye tissue in relation to a LASIK eye procedure. Here the blade is used in an automated instrument that is commonly referred to as a microkeratome or the like. The blade is used to cut a thin protective layer of corneal tissue from the patient's eye. Typically the cut is made such that this tissue remains attached to the patient's eye, and thus it is commonly referred to as a "flap." Positioning the flap away from the underlying area (e.g., by a pivotal-like motion about the remaining interconnection with the patient's eye) exposes the desired portion of the patient's cornea. A laser is then used to remove tissue from the patient's cornea or to otherwise "shape" the cornea to address associated refractive errors. Thereafter the flap is placed back in its original position. Within a few minutes the flap reattaches to the patient's eye, without the use of sutures.

Conventional microkeratome blades are stainless steel. There are a number of issues with these types of blades. One is that the blade edge is typically examined under a microscope before being used in a LASIK procedure in an attempt to identify deficiencies in the blade edge. Various discontinuities (e.g., burrs) may exist along the blade edge based upon the way in which the blade edge is formed (e.g., mechanical grinding, polishing) and the material from which the blade is formed, as well as because of the vulnerability of the cutting edge after being formed. Certain deficiencies associated with the blade edge may adversely affect the performance of the blade in cutting the eye flap for a LASIK procedure. Another is that the blade edge of conventional stainless steel microkeratome blades will typically degrade after cutting a single eye flap. Nonetheless, a common practice is to use the same microkeratome blade to cut a flap on both of the patient's eyes in a single office visit where the LASIK procedure is performed on each eye.

Most microkeratome blades are mounted on a blade handle, that is in turn mounted on a head assembly of the microkeratome. How the microkeratome blade is aligned to the blade handle can have a significant impact on the blade's cutting performance when installed on the microkeratome. Certain conventional stainless steel microkeratome blades have a mark on a surface thereof where the blade handle must be optically aligned therewith. Other conventional stainless steel microkeratome blades have holes that extend through the body of the blade. The corresponding blade handle has pins that are disposed within these holes. How these alignment marks or holes are formed on the cutting blade may have an impact on the accuracy with which the cutting edge of the blade is disposed relative to a reference surface of the blade handle. This in turn will affect the accuracy of the positioning of the blade's cutting edge when installed in the microkeratome.

Other types of microkeratome blades have been proposed. One is diamond in which a crystal is typically cleaved to define a cutting edge. Another is silicon. Both isotropic and anisotropic etches have been suggested as options for fabricating a cutting edge for a microkeratome blade or the like from a silicon wafer. Notwithstanding the recognition of these various types of options in the art, stainless steel microkeratome blades still dominate the market. In fact, the inventors associated with the subject patent application do not have knowledge of any silicon microkeratome blade that is commercially available.

There are of course many other types of applications where a blade is used to cut biological tissue (e.g., hand-held surgical instruments, scalpels), as well as many other types of non-biological cutting applications. One or more of these cutting applications may benefit from the ability to effectively fabricate cutting blades in a batch-type process using an anisotropic etch. Certain cutting applications may benefit from the ability to more accurately align the blade's cutting edge to an alignment surface on a blade handle to which the blade is mounted. Still other cutting applications may benefit from the ease with which a blade angle may be selected for the desired application and then fabricated using an anisotropic etch.

BRIEF SUMMARY OF THE INVENTION

The present invention generally relates to a method of assembling a cutting tool. One fixture (hereafter a "first fixture") is used to mount a blade handle on one or more blades that are formed on the wafer. In this regard, a first blade handle is mounted on a first blade while the wafer is positioned on the first fixture. The wafer is removed from the first fixture after a blade handle has been mounted on at least one of the blades of the wafer. Thereafter, the wafer is positioned on a different fixture (hereafter a "second fixture"). At least one blade with a handle mounted thereon is separated from a remainder of the wafer while the wafer is positioned on the second fixture.

Various refinements exist of the features noted in relation to the present invention. Further features may also be incorporated in the present invention as well. These refinements and additional features may exist individually or in any combination. The wafer may be disposed within a recess that is formed on an upper surface of both the first and second fixtures. A perimeter of each of these recesses may at least substantially approximate a perimeter of the wafer. Less than an entirety of a lower surface of the wafer is physically engaged by both the first and second fixtures in one embodiment.

Biasing forces may be exerted on the wafer while positioned on both the first and second fixtures. In one embodiment, the wafer is attracted or biased toward the first and second fixtures when positioned thereon. One way in which this may be done is by applying a suction force to at least a portion of a surface of the wafer that projects toward or faces the relevant first or second fixture (e.g., utilizing a vacuum). Preferably, the wafer is forcibly retained against the first fixture while mounting the first blade handle on the first blade. Similarly, preferably the wafer is forcibly retained against the second fixture while separating the first blade from the remainder of the wafer.

A first cutting edge of the first blade may be maintained in spaced relation to the first fixture for at least a portion of the time that the wafer is positioned on the first fixture. That is, the first cutting edge of the first blade does not contact the first fixture at least for a portion of the time that the wafer is positioned on the first fixture. In one embodiment, a first cutting edge cavity may be formed on an upper surface of the first fixture and sized/configured so as to be aligned (e.g., vertically) with the first cutting edge of the first blade when the wafer is positioned on the first fixture. Disposing the first cutting edge over the first cutting edge cavity thereby provides the desired spacing between the first cutting edge and the first fixture. The spacing between the first cutting edge and the first fixture may be maintained throughout the entire time that the wafer is positioned on the first fixture. Therefore, the first cutting edge may be maintained in spaced relation with the first fixture as the first blade handle is being mounted on the first blade.

The wafer utilized in relation to the first aspect may include a first score for at least facilitating the separation of the first blade from the wafer when positioned on the second fixture and as will be discussed in more detail below. The first fixture may support the wafer at a location that is directly under the first score. Another way of characterizing how the first fixture supports the wafer in relation to this first score is that the first fixture may support the wafer such that mounting the first blade handle on the first blade does not result in any net moment or torque about this first score. After the first blade handle has been mounted on the first blade, the wafer may be removed from the first fixture and the first blade may be separated from the wafer at least generally along this first score using the second fixture. Separation of the first blade from the wafer may be enhanced by aligning the first score with a predetermined crystal plane of the wafer.

The first blade may be disposed on a free end of what may be characterized as a first blade support tab or first cantilever. One end of this first cantilever is fixed or anchored (e.g., stationary relative to an adjoining portion of the wafer), while its opposite end (the noted free end on which the first blade is disposed) is movable at least generally about the fixed end of the first cantilever at the appropriate time (e.g., when separating the first blade from the wafer in the above-noted manner). At least a portion of this first cantilever may be supported by the first fixture while the first blade handle is being mounted on the first blade. This then reduces the potential for a movement of the first blade toward the first fixture while mounting the first blade handle on the first blade. There is preferably no deflection of the free end of the first cantilever toward the first fixture while mounting the first blade handle on the first blade.

Preferably the first blade handle is maintained in fixed relation to the first blade after being mounted thereon. Any appropriate way of anchoring the first blade handle to the first blade may be utilized. However, in one embodiment an adhesive is applied to at least one of the first blade handle and the first blade prior to mounting the first blade handle on the first blade. Light curable adhesives are preferred such that the position of the first blade handle may be adjusted after establishing an initial contact between the first blade handle and the first blade via the intermediary adhesive. Once the first blade handle is in the desired/required position relative to the first blade, a light source may be activated to cure or set the adhesive to thereafter maintain the first blade handle in fixed relation to the first blade. Stated another way, the preferred adhesive is one having a set or cure time that will allow the first blade handle to be moved into the desired/required position after being initially seated on the first blade.

The surface of the first fixture may be configured such that no portion of the first blade handle contacts the first fixture while mounting the first blade handle on the first blade, and more preferably throughout the entire time that the wafer is positioned on the first fixture. In one embodiment, a first registrant extends from a lower surface of the first blade handle and a first registration cavity is accessible through an upper surface of the first blade. Mounting the first blade handle on the first blade may then entail directing the first registrant of the first blade handle at least within this first registration cavity of the first blade. An open space may separate the lower extreme of the first registrant and the first fixture after the first blade handle is mounted on the first blade. This may be provided by aligning the first registrant with a first registrant cavity that is formed on a surface of the first fixture that projects toward or faces the wafer such that this end of the first registrant is disposed in spaced relation with the first fixture at all times, and thereby including after the first blade handle is mounted on the first blade.

One embodiment of the present invention is directed toward having first and second registrants extend from a lower surface of the first blade handle in combination with first and second registration cavities that are accessible through an upper surface of the first blade. Mounting the first blade handle on the first blade may then entail disposing the first registrant of the first blade handle at least within this first registration cavity of the first blade, and disposing the second registrant of the first blade handle at least within this second registration cavity of the first blade. An open space may separate the lower extreme of both the first and second registrants and the first fixture after the first blade handle is mounted on the first blade. First and second registrant cavities may be formed on an upper surface of the first fixture in alignment with the first and second registrants, respectively, to provide the desired spacing. In one embodiment, the first fixture supports the wafer at least at a location that is between the first and second registration cavities of the first blade.

Mounting the first blade handle on the first blade may entail disposing the first blade handle on an upper surface of the first blade (e.g., so that the first blade then entirely supports the first blade handle), thereafter moving the first blade handle relative to the first blade, and terminating this movement when a first registration feature (e.g., a first registrant) of the first blade handle contacts a first registration feature (e.g., a first registration surface) of the first blade (e.g., a mechanical registration), or so as to register the first blade handle to the first blade. In one embodiment, the first blade handle is moved in a first direction to in effect seat a lower surface of the first blade handle on an upper surface of the first blade, and the first blade handle is thereafter moved in a second direction that is perpendicular to this first direction to achieve the desired registration. Movement of the first blade handle relative to the first blade until the desired registration has occurred may also be characterized as moving the first blade handle at least generally away from a first cutting edge of the first blade or toward a rear end of the first blade. Another characterization of the movement of the first blade handle relative to the first blade to achieve the desired registration is that the first blade handle moves relative to the first blade along a path that is parallel with the upper surface of the first blade on which the first blade handle is in effect seated. In any case, the first blade handle is preferably fixed or anchored to the first blade after the desired registration is achieved.

Multiple first blades may be formed on the wafer prior to being positioned on the first fixture. A first blade handle may be mounted on each first blade in the above-described manner. First blade handles may be sequentially mounted on the various first blades, multiple first blade handles may be simultaneously mounted on multiple first blades, or first blade handles may be simultaneously mounted on all first blades formed on the wafer. Regardless of how many first blades are formed on the wafer and the sequence of installing any first blade handle(s) thereon, the wafer may be removed from the first fixture with a first blade handle being mounted on at least one first blade and with the first blade(s) remaining part of the first wafer. That is, after a first blade handle has been mounted on at least one first blade, the wafer may be removed from the first fixture and without having separated any such first blade (with a first blade handle mounted thereon) from the wafer. Thereafter, the various individual first blades with a first blade handle mounted thereon may be separated from the remainder of the wafer using the second fixture that will now be discussed.

One way to characterize how the second fixture may support the wafer is that it may do so with the first blade being suspended above the second fixture so as to not be in contact therewith. In this regard, the first blade may be disposed on a free end of what may be characterized as a first blade support tab or first cantilever. One end of this first cantilever may extend from what may be characterized as a wafer frame. This "wafer frame" may be viewed as the remainder of the wafer in relation to each first blade and corresponding first cantilever formed from the wafer, and preferably does not itself include any cantilevered structure. In any case, an opposite end of the above-noted first cantilever (the noted free end on which the first blade is disposed) is movable at least generally about the fixed end of the first cantilever (e.g., that which merges with the wafer frame). At least a portion of this first cantilever may be supported by the second fixture, while the first blade remains in spaced relation to the second fixture to await separation.

A first cutting edge of the first blade may be disposed in spaced relation to the second fixture for at least a portion of the time that the wafer is positioned on the second fixture. That is, the first cutting edge of the first blade does not contact the second fixture at least for a portion of the time that the wafer is positioned on the second fixture. Preferably, the first cutting edge never contacts either the first or second fixture. In any case, a first cutting edge cavity may be formed on an upper surface of the second fixture and sized/configured so as to be aligned (e.g., vertically) with the first cutting edge of the first blade when the wafer is positioned on the second fixture. Disposing the first cutting edge over the first cutting edge cavity thereby provides the desired spacing between the first cutting edge and the second fixture. The spacing between the first cutting edge and the second fixture may be maintained throughout the entire time that the wafer is positioned on the second fixture. Therefore, the first cutting edge may be maintained in spaced relation with the second fixture prior to, during, and after the first blade is separated from the remainder of the wafer.

Separation of the first blade from a remainder of the wafer may include fracturing the wafer. This separation may be at least substantially along a line that is at least substantially parallel with the first cutting edge of the first blade. A first score in the wafer may be utilized for this separation. The wafer may be fractured at least generally along this first score to at least facilitate the separation of the first blade from the remainder of the wafer. In one embodiment, the second fixture is configured to support the wafer proximate to this first score and yet maintain the first blade in spaced relation to the first fixture.

Deflection of the first blade at least generally toward the second fixture may be utilized to achieve separation of the first blade from the remainder of the wafer. Any such deflection need not be of the entire first blade, but may be limited to only a portion of the first blade. Moreover, not all portions of the first blade need to deflect the same amount in the general direction of the second fixture.

The first blade handle is already mounted on the first blade at the time that it is separated from the remainder of the wafer. In one embodiment, a force is exerted directly on the first blade handle and at least generally in a direction of the second fixture to separate the first blade from the remainder of the wafer. In another embodiment, a force is exerted directly on the first blade and at least generally in a direction of the second fixture to separate the first blade from the remainder of the wafer.

As noted above, the entire first blade may be disposed in spaced relation to the second fixture when the wafer is positioned on the second fixture and while the first blade is still part of the wafer. The first blade may be separated from the remainder of the wafer while still being spaced from the second fixture. That is, prior to any portion of the first blade establishing contact with the underlying second fixture in a manner discussed in more detail below, the first blade may separate from the remainder of the wafer as a result of the exertion of a force on the first blade (directly or indirectly through the above-noted first blade handle) that is again at least generally directed toward the second fixture.

Contact may be established between the first blade and the second fixture after the first blade has separated from the remainder of the wafer. However, the first cutting edge of the first blade still preferably remains in spaced relation to the second fixture. In one embodiment, the first blade is directed onto what may be characterized as a horizontal beam that traverses the first blade (e.g., disposed parallel with but spaced from its first cutting edge) and that is recessed relative to a surface of the second fixture that supports the wafer on the second fixture. At this time the first cutting edge of the first blade may be disposed over what may be characterized as a cutting edge cavity formed on the upper surface of the second fixture, while a rear edge may be disposed over what may be characterized as a pivot cavity formed on the upper surface of the second fixture. A rearward portion of the first blade may then be directed into the pivot cavity by a pivoting-like or teeter-totter-like action of the first blade about the recessed horizontal beam. This of course increases the spacing between the first cutting edge of the first blade and the second fixture, while decreasing the spacing between a rear end of the first blade and the second fixture. Therefore, the first cutting edge of the first blade may actually first move toward the second fixture as the first blade is being separated from the remainder of the wafer (preferably without contacting the second fixture as the first cutting edge is again preferably disposed over a first cutting edge cavity formed on the upper surface of the second fixture), and then back away from the second fixture after the first blade starts to pivot about the noted horizontal beam. Once again, preferably the first cutting edge of the first blade never contacts the second fixture the entire time that the wafer is positioned on the second fixture.

The first blade may seat against an inclined surface formed on the upper surface of the second fixture after the first blade has separated from the remainder of the wafer.

This inclined surface may define a portion of a boundary of the above-noted pivot cavity. In any case, a rear end of the first blade will be disposed at a lower elevation than its first cutting edge when the first blade is seated against this inclined surface. Biasing forces maybe exerted on the first blade to retain the same against this inclined surface. In one embodiment, the first blade is attracted or biased toward the second fixture after being separated from the remainder of the wafer. One way in which this may be done is by applying a suction force to at least a portion of a lower surface of the first blade that interfaces with the inclined surface (e.g., utilizing a vacuum).

Multiple first blades may be formed on the wafer prior to being positioned on the second fixture. A first blade handle may be mounted on each first blade as well before the wafer is positioned on the second fixture. First blades may be sequentially separated from the remainder of the wafer in the above-noted manner, multiple first blades may be simultaneously separated from the remainder of the wafer in the above-noted manner, or all first blades formed on the wafer may be simultaneously separated from the remainder of the wafer in the above-noted manner. Regardless of how many first blades are formed on the wafer and the sequence of separating first blades from the remainder of the wafer, the wafer may be removed from the second fixture after at least one first blade has been separated from the remainder of the wafer. All first blades are preferably separated from the wafer prior to removing the wafer from the second fixture. However, any first blade that has been separated from the remainder of the wafer may be removed from the second fixture prior to or after the wafer is removed from the second fixture.

BRIEF DESCRIPTION OF THE SEVERAL VIEWS OF THE DRAWING

FIG. 2B is a top view of the cutting blade of the cutting tool utilized by the microkeratome of FIG. 1.

FIG. 3A is a cross-sectional view of the cutting blade of FIG. 2B take along line 3—3.

FIG. 3B is a cross-sectional view of an alternative embodiment of a cutting blade, namely in relation to the definition of its cutting edge in relation to that illustrated in FIG. 3A.

DETAILED DESCRIPTION OF THE INVENTION

Figure 1:
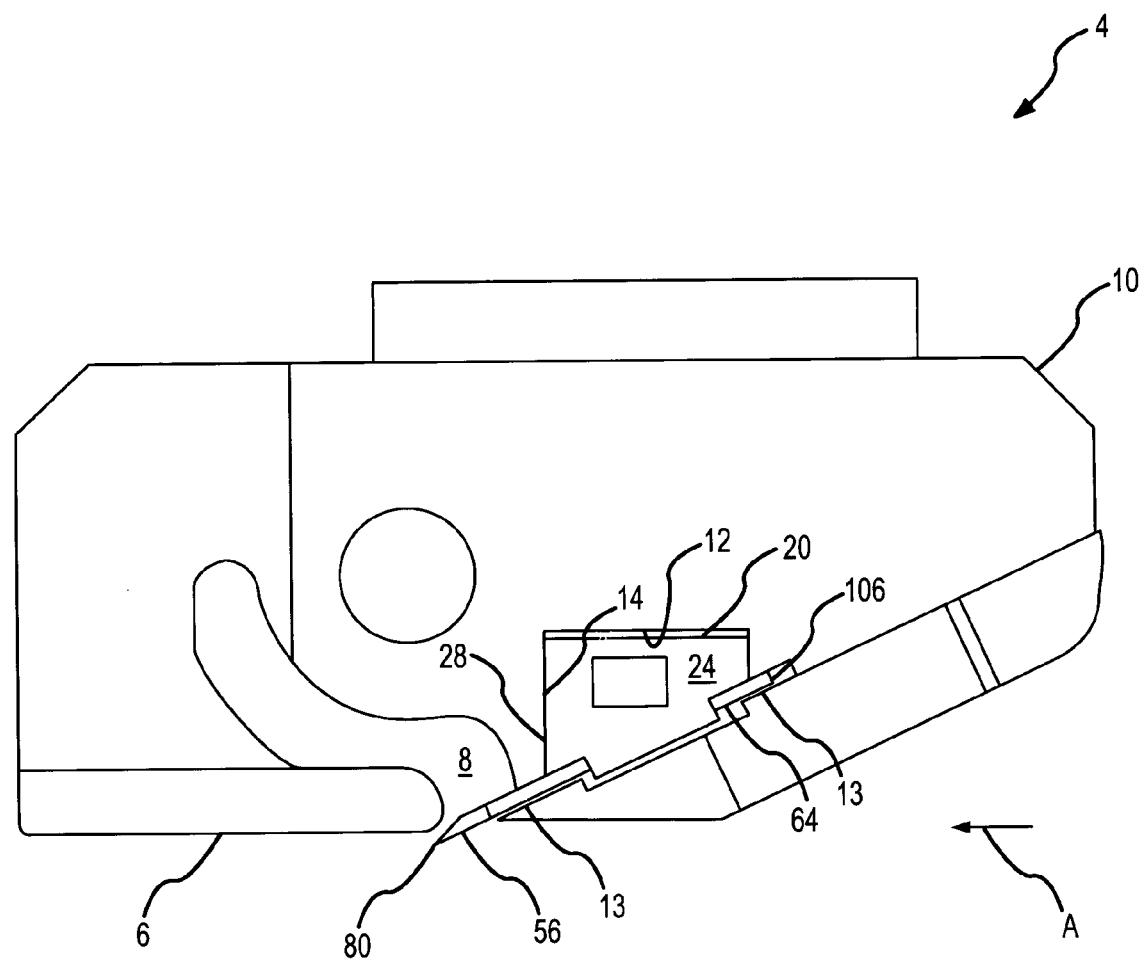
FIG. 1 is a side view of one embodiment of a microkeratome.

The present invention will now be described in relation to the accompanying drawings which at least assist in illustrating its various pertinent features. A schematic of one embodiment of a microkeratome 4 that may be used to perform a LASIK procedure on a patient's eye (not shown) is illustrated in FIG. 1. The microkeratome 4 generally includes a head assembly 10 having a presser 6, a cut flap receiver 8, and a cutting tool receiver 12 with a cutting tool 20 disposed therein. Generally, the presser 6 pushes down on the front of the patient's eye while the cutting tool 20 is brought into engagement with and cuts a flap from the patient's eye. Cutting operations generally entail moving the cutting tool 20 in an appropriate manner relative to the patient's eye (e.g., by oscillation of the cutting tool 20 relative to the head assembly 10 in a direction that is parallel with a cutting edge 80 associated with the cutting tool 20 (in and out of the page in the view presented in FIG. 1), as well as by a movement of the head assembly 10 in the direction of the arrow A). In any case, the resulting eye flap (with a portion typically still remaining attached to the patient) is then directed into the cut flap receiver 8 formed in the head assembly 10 of the microkeratome 4.

There are two primary components of the cutting tool 20, namely a blade handle 24 and a cutting blade 56. The cutting blade 56 includes the above-noted cutting edge 80. This cutting edge 80 is formed on its forward end. The blade handle 24 interfaces with the cutting blade 56 so as to desirably align or register the position of the cutting edge 80 of the blade 56 with a microkeratome registration surface 28 of the blade handle 24 with enhanced accuracy. This microkeratome registration surface 28 in turn interfaces with a cutting tool registration surface 14 associated with the head assembly 10 of the microkeratome 4. More specifically, the cutting tool 20 is disposed within a cutting tool receiver 12 formed within the head assembly 10. A pair of support surfaces 13 of the head assembly 10 engage corresponding portions of a bottom surface 64 of the cutting blade 54 to "vertically" support the cutting blade 56 (shown in slightly vertically spaced relation in FIG. 1 for clarity), while other portions of this bottom surface 64 of the cutting blade 56 are disposed and maintained in spaced relation to the underlying portion of the head assembly 10. Moreover, the microkeratome registration surface 28 of the blade handle 24 engages the cutting tool registration surface 14 of the head assembly 10 of the microkeratome 4. Because the position of the cutting edge 80 is registered relative to the microkeratome registration surface 28 of the blade handle 24, and because the position of the microkeratome registration surface 28 of the blade handle 24 is registered relative to the cutting tool registration surface 14 of the head assembly 10 of the microkeratome 4, the position of the cutting edge 80 of the blade 56 is likewise registered relative to this cutting tool registration surface 14. Enhancing the accuracy of the positioning of the cutting edge 80 for a LASIK procedure is of course very desirable.

Figure 2A:
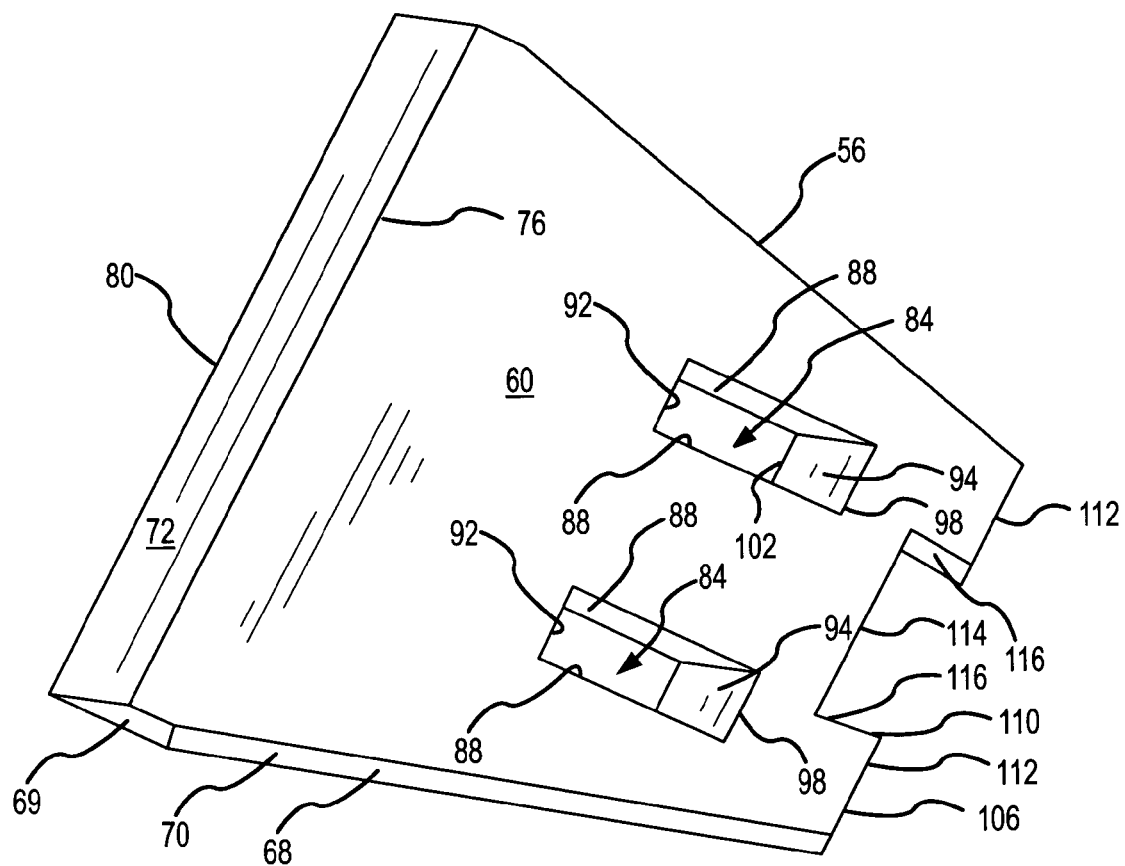
FIG. 2A is a top-based perspective view of a cutting blade of the cutting tool utilized by the microkeratome of FIG. 1.

Additional views of the cutting blade 56 are presented in FIGS. 2A–B and 3A. The cutting blade 56 includes a top wall or surface 60 and a bottom wall or surface 64. A pair of side walls or surfaces 68 of the cutting blade 56 are laterally spaced from a central, longitudinal reference axis 58 associated with the cutting blade 56. Herein, the term "laterally" spaced, extending, or the like means being at least generally in or along a direction that is perpendicular to the central, longitudinal reference axis 58 of the blade 56. Longitudinally spaced from the cutting edge 80 of the cutting blade 56 is a rear wall or surface 106. Herein, the term "longitudinally" spaced, extending, or the like means being at least generally in or along a direction that is collinear with or parallel to the central, longitudinal reference axis 58 of the blade 56. Both the side surfaces 68 and the rear surface 106 extend between and interconnect the top surface 60 and bottom surface 64 of the blade 56. The distance between the top surface 60 and the bottom surface 64 thereby defines a thickness of the cutting blade 56. In one embodiment, the thickness of the cutting blade 56 is within a range of about 230 microns to about 250 microns.

The rear surface 106 of the blade 56 includes a notch or recess 110 that is centrally disposed relative to the central, longitudinal reference access 58. In this regard, the rear surface 106 includes what may be characterized as a pair of first sections 112, a second section 114 that is longitudinally spaced from the first section 112 in the direction of the cutting edge 80, and a pair of laterally spaced third sections 116 that interconnect the second section 114 with one of the first sections 112. Generally, the configuration of the rear surface 106 facilitates the removal of the cutting blade 56 from a wafer from which a plurality of cutting blades 56 may be fabricated in a batch process. This will be discussed in more detail below.

In the illustrated embodiment of the cutting blade 56: 1) each side surface 68 includes a first section 69 that extends rearwardly from the cutting edge 80 perpendicularly thereto, as well as a second section 70 that extends rearwardly from its corresponding first section 69 and at least generally toward the central, longitudinal reference axis 58; 2) the pair of first sections 112 and the second section 114 associated with the notch 110 on the rear surface 106 are all parallel with the cutting edge 80; and 3) the pair of laterally spaced (relative to the central, longitudinal reference axis 58) third sections 116 associated with the notch 110 are parallel with the central, longitudinal reference axis 58. Other configurations for the cutting blade 56 may be appropriate depending upon the application, as well as other configuration/orientations for the various parts thereof unless otherwise noted herein as being required.

A planar first cutting edge surface 72 is disposed at an angle relative to the top surface 60 of the blade 56 and intersects with this top surface 60 at an upper edge 76. The first cutting edge surface 72 extends between this upper edge 76 and the cutting edge 80 of the cutting blade 56. In the illustrated embodiment, the first cutting edge surface 72 also intersects with the bottom surface 64 of the cutting blade 56. As such, that portion of the bottom surface 64 of the cutting blade 56 that is adjacent to the cutting edge 80 and intersects with the first cutting edge surface 72 may be characterized as a second cutting edge surface 66 for the cutting blade 56. The first cutting edge surface 72 is disposed at an angle $\theta$ (FIG. 3A) relative to the second cutting edge surface 66, and this may be characterized as the blade angle $\theta$. Any appropriate blade angle $\theta$ may be utilized by the cutting blade 56 and which may depend upon the application in which the blade 56 is to be used. In one embodiment for the case of biological applications (e.g., cutting tissue, such as a human eye), the blade angle $\theta$ is preferably within a range of about 15° to about 25°.

Other options exist for defining the cutting edge 80 and the blade angle θ of the cutting blade 56. One example is presented in FIG. 3B where the cutting edge 80' is defined by a second cutting edge surface 66' that is disposed at an angle relative to the bottom surface 64 of the blade 56' and that intersects with the first cutting edge surface 72'. This of course disposes the cutting edge 80' at what may be characterized as an "intermediate elevation" between the elevation of the top surface 60 and the elevation of the bottom surface 64 of the cutting blade 56'.

Features are incorporated into the structure of the cutting blade 56 for purposes of registering or aligning the cutting edge 80 to a particular position when installed on the microkeratome 4. These same features are incorporated in each cutting blade 56 so that the cutting edge 80 of each cutting tool 20 that is installed in the microkeratome 4 is registered or aligned to the same position, preferably within a tolerance of 25 microns. That is, the variance of the position of the cutting edge 80 relative to the desired position is no more than about 25 microns in any dimension for each cutting tool 20 that may be installed in the microkeratome 4. This variation principally relates to the geometry of the blade handle 24 and the adhesion of the blade handle 24 to the cutting blade 56.

The cutting blade 56 includes a pair of registration cavities 84 that interface or cooperate with the blade handle 24 in a manner so as to register or align the cutting edge 80 to the desired position when installed in the microkeratome 4. Any appropriate number of registration cavities 84 may be utilized and disposed in any appropriate position on the cutting blade 56. However, utilizing a pair of registration cavities 84 in the position of the illustrated embodiment provides a number of advantages, including facilitating parallel orientation of the blade handle 24 relative to the cutting edge 80 of the blade 56.

Both registration cavities 84 of the cutting blade 56 are identical. Only one registration cavity 84 then need be described herein. The registration cavity 84 extends through the entire thickness of the cutting blade 56 in the illustrated embodiment, although such may not be required for all applications that may utilize the blade 56 or cutting tool 20. For instance, the registration cavity 84 could be formed on the top surface 60 of the blade 56 and extend down toward, but not to, the bottom surface 64. However, preferably the "bottom" of the registration cavity 84 (more specifically a lower edge 102 of a registration wall or surface 94 associated with the registration cavity 84) and the cutting edge 80 are disposed at the same elevation or distance from the top surface 60 (measured perpendicularly to the top surface 60). In any case, the registration cavity 84 may be characterized as being at least generally concave or "upwardly open" in relation to the top surface 60 of the cutting blade 56 (e.g., accessible through the top surface 60 of the blade 56).

Each registration cavity 84 includes a front wall 92, a rear wall or registration surface 94 that is longitudinally spaced from the front wall 92, and a pair of laterally spaced side walls 88 that extend between and interconnect the front wall 92 with the registration surface 94. Generally, the front wall 92 and side walls 88 of the registration cavity 84 may be of any appropriate shape/configuration/orientation, as it is the registration surface 94 that provides the desired registration in relation to the cutting edge 80. How far the registration surface 94 and the corresponding front wall 92 should be longitudinally spaced (represented by distance "S" in FIG. 8B) is at least by a distance that would allow the blade handle 24 to first be installed on the cutting blade 56, and then moved parallel with the top surface 60 of the cutting blade 56 to register or align the blade handle 24 relative to the cutting blade 56 using the registration surface(s) 94. The spacing between the side walls 88 of the registration cavities 84 may provide a "lateral" registration feature for the blade handle 24 relative to the cutting blade 56 as will be discussed in more detail below.

Registration or alignment of the cutting edge 80 relative to the microkeratome registration surface 28 of the blade handle 24, and thereby relative to the cutting tool registration surface 14 of the head assembly 10 of the microkeratome 4, is provided in the case of the cutting blade 56 by having the registration surface 94 be a planar surface that is parallel with the planar first cutting edge surface 72. That is, the registration surface 94 of each registration cavity 84 utilized by the cutting blade 56 is a planar surface that extends from an upper edge 98 (at the intersection with the top surface 60 in the illustrated embodiment) to a lower edge 102 (at the intersection with the bottom surface 64 in the illustrated embodiment) in the same orientation that the planar first cutting edge surface 72 extends from its upper edge 76 to the cutting edge 80. The lower edge 102 of each registration cavity 84 is parallel with the cutting edge 80. In the illustrated embodiment, the upper edge 76 of the first cutting edge surface 72 and the upper edge 98 of each registration surface 94 are disposed within a first reference plane that is parallel with a second reference plane, that in turn contains the cutting edge 80 associated with the first cutting edge surface 72 and the lower edge 102 of each registration surface 94 (and parallel with the top surface 60 and bottom surface 64 of the blade 56 for that matter). Moreover, the pair of registration surfaces 94 of the registration cavities 84 are disposed within a common reference plane. As such, the registration cavities 84 are disposed equidistantly from the cutting edge 80, as are their corresponding registration surfaces 94.

One preferable way to fabricate the cutting blade 56 is by using an anisotropic etch, at least for purposes of defining the first cutting edge surface 72 and the registration surface 94 of each registration cavity 84. Preferably the entire cutting blade 56 is defined by a single anisotropic etch. This allows the various structures to be very precisely positioned. For instance, the registration cavities 84 may be very precisely positioned relative to the cutting edge 80. The maximum variation in the location of the cutting edge 80 relative to the lower edge 102 of each registration cavity is about 6 microns. This variation may be influenced by a number of factors. Referring to FIG. 2A, the upper edge 76 of the first cutting edge surface 72 and the upper edge 98 of each registration cavity 84 are formed to within a tolerance of 1 micron or better. This is due to the fact that they may be defined using the same photolithographic mask as will be discussed in more detail below in relation to FIGS. 9A–D and FIG. 10. FIGS. 9A–D and FIG. 10 are specifically directed to the fabrication of the cutting blade 56. Any variation in the location of the first cutting edge surface 72 relative to the registration surface 94 of each registration cavity 84 would be due to errors in the position of one or more of the upper edge 76 of the first cutting edge surface 72 and the upper edge 98 of each registration cavity 84, coupled with errors associated with the etch process. However, any variation in the location of the first cutting edge surface 72 relative to the registration surface 94 of each registration cavity 84 should be no more than about 2 microns. This in turn will then influence the location of the cutting edge 80 relative to the lower edge 102 of each registration cavity 84, as will the geometry of the planes that intersect to form the edges 80, 76, 98, and 102. Once again, the maximum variation between the location of the cutting edge 80 relative to, the lower edge 102 of each registration cavity 84 should be no more than about 6 microns for a blade angle θ of 19 degrees that will be discussed in more detail below (e.g., 2 microns, divided by the sine of 19 degrees).

Figure 2C:
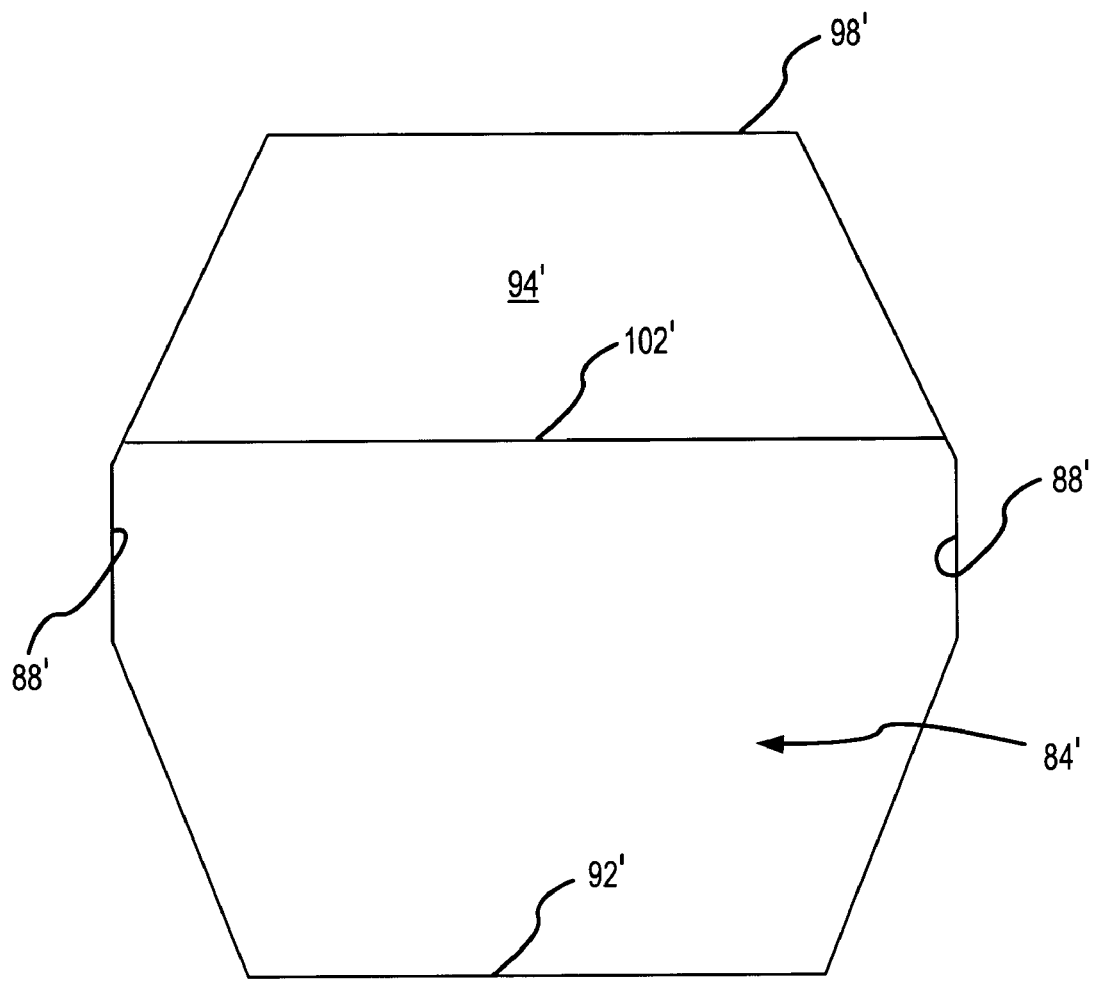
FIG. 2C is a plan view of a modified registration cavity that may be used by the cutting blade of FIGS. 2A–B.
Figure 4:
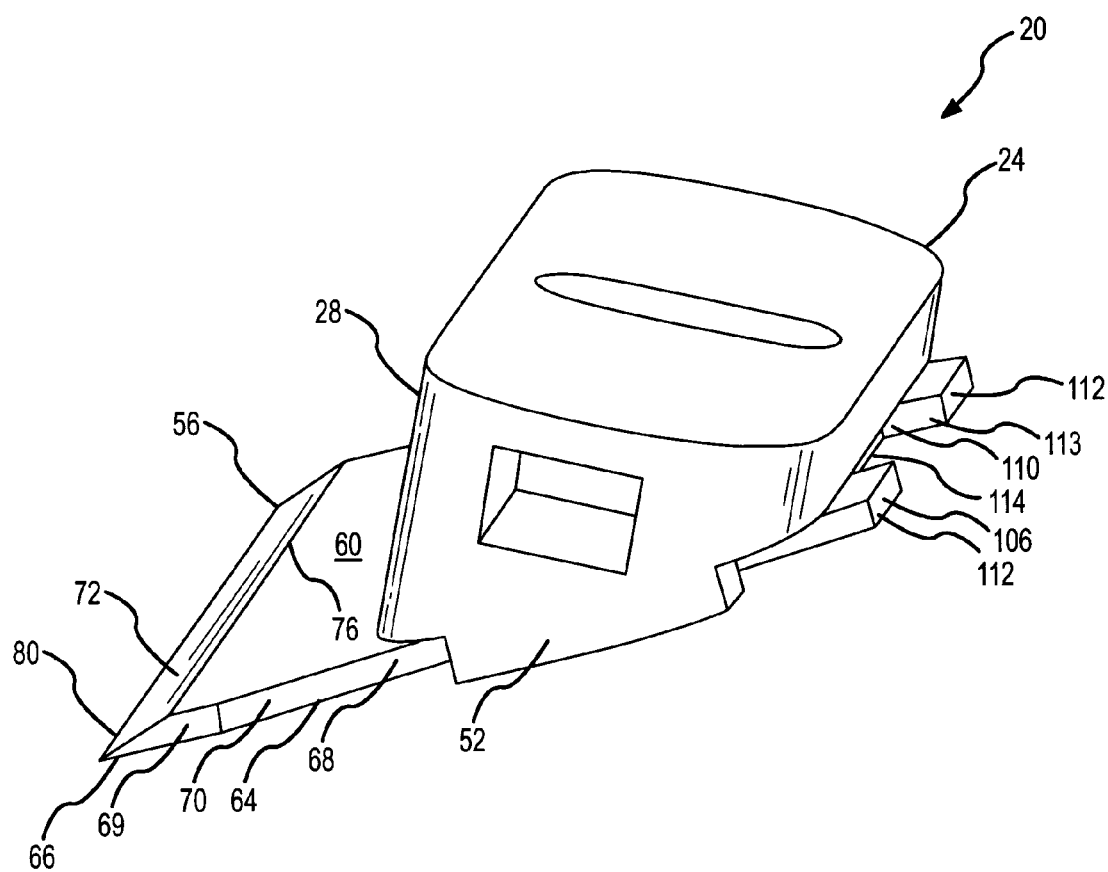
FIG. 4 is a side-based perspective view of the cutting tool utilized by the microkeratome of FIG. 1.
Figure 5:
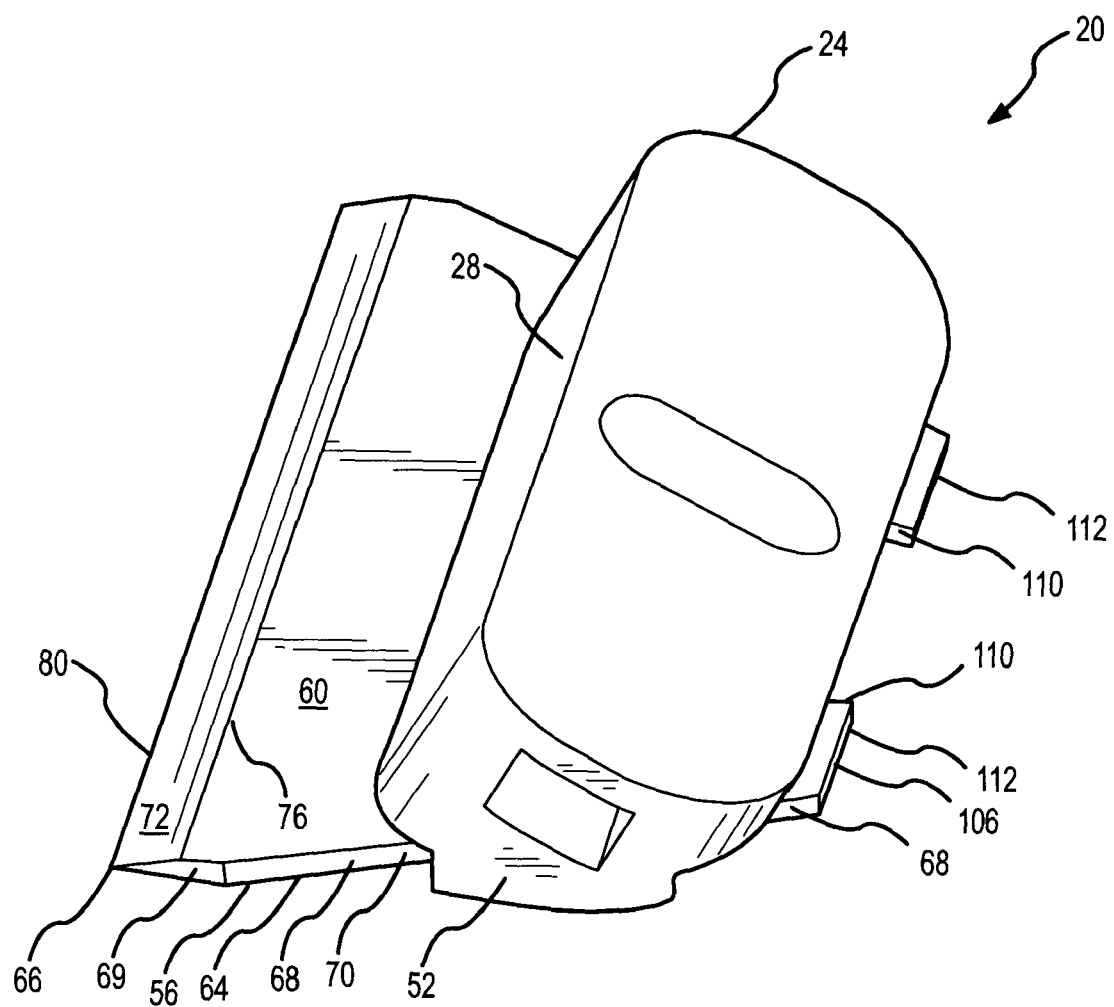
FIG. 5 is a top-based perspective view of the cutting tool utilized by the microkeratome of FIG. 1.
Figure 6:
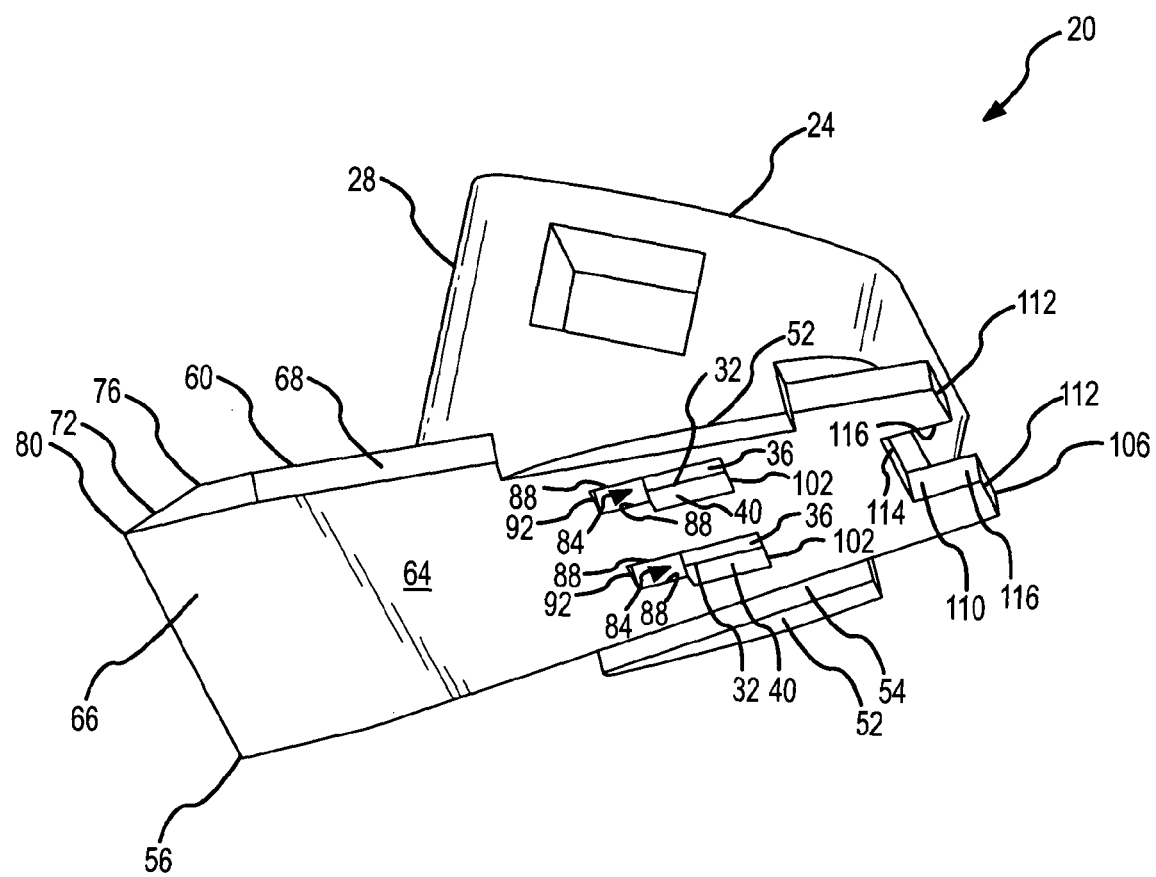
FIG. 6 is a bottom-based perspective view of the cutting tool utilized by the microkeratome of FIG. 1.
Figure 7:
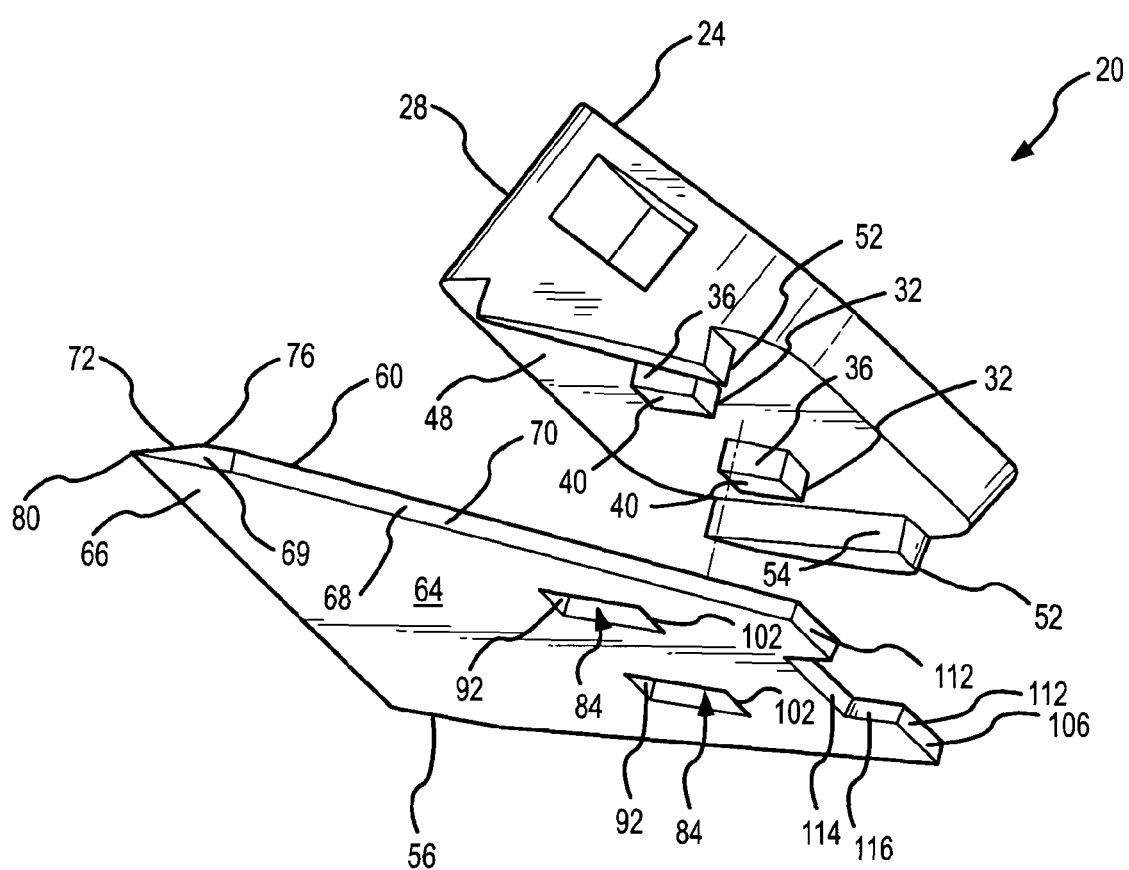
FIG. 7 is an exploded, perspective view of the cutting tool utilized by the microkeratome of FIG. 1.

It should be appreciated that the structure of the blade 56 set forth herein is "idealized" in accordance with its corresponding blade mask as noted above, and therefore that the resulting shape of the various components of the blade 56 may not conform exactly to the illustrations provided herein. For instance, FIGS. 2A–B illustrate the shape of the registration cavities 84 in accordance with the blade mask. The anisotropic etch may actually produce a profile that is illustrated in FIG. 2C, where a "single prime" designation again is used to identify an alternative configuration for the registration cavity 84' (along with its corresponding upper edge 98', registration surface 94', lower edge 102', side walls 88', and front wall 92').

There are a number of features of the cutting blade 56 that accommodate or relate in at least some manner to using an anisotropic etch fabrication technique for the blade 56. One that is key in relation to the above-described registration feature is that the first cutting edge surface 72 and the registration surface 94 of each registration cavity 84 should be coplanar or parallel with a common crystal plane that the selected anisotropic etchant will etch to, but not through. In one embodiment where the anisotropic etchant is KOH and where the cutting blade 56 is etched from single crystal silicon, the first cutting edge surface 72 and the registration surface 94 of each registration cavity 84 are coplanar or parallel with a plane in the {111} family of planes (which includes both the positive and negative intercepts). That is, a plane within the {111} family of planes in effect is an etch stop for the anisotropic etch. Other crystal planes could be selected for the first cutting edge surface 72 and the registration surface 94 of each registration cavity 84. However, an appropriate anisotropic etchant must of course be selected for the material being etched and the crystal plane that is to be used to define the orientation of the first cutting edge surface 72 and the registration surface 94 of each registration cavity 84 in the described manner.

Both the top surface 60 and the bottom surface 64 of the cutting blade 56 should be planar surfaces, including for purposes of accommodating using an anisotropic etchant to define the first cutting edge surface 72 and the registration surface 94 of each registration cavity 84. Flexibility in relation to the definition of the cutting edge 80, more specifically in relation to its associated blade angle θ (FIG. 3A), may be realized by forming the top surface 60 and bottom surface 64 of the cutting blade 56 in a certain manner. At least one Miller index of the set of three Miller indices that define the top surface 60 and the bottom surface 64 of the cutting blade 56 should have an absolute value greater than "3" and be within the family of planes defined by the set of three Miller indices {ABC}, where "A", "B", and "C" each represent one Miller index, where at least one of the three indexes has an absolute value greater than "3", and where "A", "B", and "C" each include both the positive and negative intercepts.

Each of the side surfaces 68 of the cutting blade 56, the front wall 92 and pair of side walls 88 of each registration cavity 84, and the rear surface 106 of the cutting blade 56 may be of any orientation relative to the top surface 60 and bottom surface 64 of the cutting blade 56. In one embodiment and for the case where the cutting blade 56 is fabricated from single crystal silicon: the front wall 92 of each registration cavity 84 and the rear surface 106 of the cutting blade 56 are both perpendicular to the top surface 60 and bottom surface 64 of the blade 56, and further are coplanar with or parallel with a crystal plane in the {111} family of planes (including both the positive and negative intercepts); and the side surfaces 68 of the cutting blade 56 and the side walls 88 of each registration cavity 84 are not perpendicular to the top surface 60 and bottom surface 64 of the blade 56, and are not necessarily coplanar with a crystal plane in the {111} family of planes (including both the positive and negative intercepts).

Cooperation between the cutting blade 56 and the blade handle 24 of the cutting tool 20 is at least one component of registering or aligning the cutting blade 56 in a desired position relative to a patient when installed in the microkeratome 4, more specifically its cutting edge 80. Various features of the blade handle 24 are presented in FIGS. 4–7 for the case of the configuration of the head assembly 10 utilized by the microkeratome 4 of FIG. 1. It should be appreciated that other configurations for the blade handle 24 may be required for different applications of the cutting blade 56, different types of microkeratomes 4, or different head assemblies. Moreover, not all applications of the cutting blade 56 will necessarily require an "intermediate" blade handle.

The blade handle 24 is attached or anchored to the cutting blade 56 so that there is no substantial movement therebetween. Stated another way, the blade handle 24 and the cutting blade 56 function as a single unit and move together during operation of the microkeratome 4. Any appropriate way of maintaining the blade handle 24 in a fixed relative positional relationship with the cutting blade 56 may be used, including any appropriate adhesive (e.g., an epoxy; a UV curable epoxy; an epoxy with spacing spheres), or by deforming some portion of the handle 24 by melting or heat-staking.

Features may be incorporated into the structure of the blade handle 24 for interfacing with the head assembly 10 of the microkeratome 4 or otherwise. The blade handle 24 includes a pair of laterally spaced guide rails 52 in the illustrated embodiment that are disposed along a portion of the side surfaces 68 of the cutting blade 56 (more specifically the second sections 70) when the blade handle 24 is mounted on the cutting blade 56. In one embodiment, the surface 54 of each of the guide rail 52 that projects toward the corresponding portion of the side surface 68 of the cutting blade 56 is planar and disposed in parallel relation with the corresponding portion of the side surface 68 of the cutting blade 56. Other profiles may be appropriate. There may be a space between at least a portion of this surface 54 of the guide rails 52 and their corresponding side surface 68 when the blade handle 24 is registered or aligned with the cutting blade 56.

Registration or alignment of the cutting edge 80 of the cutting blade 56 in the desired position in the microkeratome 4 utilizes the microkeratome registration surface 28 of the blade handle 24. This microkeratome registration surface 28 again interfaces with the cutting tool registration surface 14 on the head assembly 10 of the microkeratome 4. Although the cutting tool registration surface 14 is disposed on the "foreword" end of the blade handle 24, it may be disposed in any appropriate position so as to cooperate with a corresponding registration surface on the head assembly 10 of the microkeratome 4.

Multiple features of the blade handle 24 relate in at least some manner to the accurate positioning of the cutting edge 80 of the cutting blade 56 relative to the blade handle 24, more specifically its microkeratome registration surface 28.

One is a planar bottom surface 48 of the blade handle 24 that interfaces with the planar top surface 60 of the cutting blade 56. This provides what may be characterized as a "vertical" registration feature between the blade handle 24 and cutting blade 56. Both a lateral and a longitudinal or "fore/aft" registration feature between the blade handle 24 and the cutting blade 56 may be provided by the blade handle 24 including at least one registrant 32. Each registrant 32 extends or projects at least generally downwardly from the planar bottom surface 48 of the blade handle 24. A pair of registrants 32 are utilized by the blade handle 24 in the illustrated embodiment, one for each registration cavity 84 of the cutting blade 56. These registrants 32 are disposed along a common line that is parallel with the cutting edge 80 of the blade 56 when the blade 56 is properly registered to the blade handle 24.

Each registrant 32 includes a peripheral wall 36 that intersects with a bottom wall 40. Four side walls or surfaces 37a–d (FIGS. 8A–B) define the peripheral wall 36 in the illustrated embodiment, with the side walls 37a and 37c being parallel with each other, and with the side walls 37b and 37d being parallel with each other. In the illustrated embodiment, the bottom wall 40 is rectangular. These four side walls 37a–d of the peripheral wall 36 of each registrant 32 are disposed perpendicular to the bottom surface 48 of the blade handle 24 in the illustrated embodiment. Lateral registration of the blade handle 24 relative to the cutting blade 56 may be provided by the having the side walls 37b and 37d of each registrant 32 be spaced apart the same distance as the side walls 88 of the corresponding registration cavity 84 in which the registrant 32 is disposed. This will then dispose the side walls 37b, 37d of a given registrant 32 in interfacing or at least closely spaced relation with the corresponding side wall 88 of the corresponding registration cavity 84. Other configurations/orientations of the peripheral wall 36 for each registrant 32 may be appropriate and provide at least a degree of lateral registration. Longitudinal registration of the blade handle 24 to the cutting blade 56 is provided by cooperation between each registrant 32 and its corresponding registration surface 94, namely that which is associated with the registration cavity 84 in which the registrant 32 is disposed.

Mounting the blade handle 24 on the cutting blade 56 may generally entail disposing an appropriate adhesive on at least one of the top surface 60 of the cutting blade 56 and the bottom surface 48 of the blade handle 24. A light curable epoxy is a particularly desirable way to attach the blade handle 24 to the cutting blade 56. Each registrant 32 on the bottom surface 48 of the blade handle 24 is then disposed within its corresponding registration cavity 84 on the cutting blade 56. Although only relative movement is required, in one embodiment the blade handle 24 is advanced toward a stationary cutting blade 56. In any case, preferably the registrants 32 are initially disposed within the corresponding registration cavity 84 so as to not contact its rear wall or registration surface 94. This may be utilized to seat the planar bottom surface 48 of the blade handle 24 on the planar top surface 60 of the cutting blade 56. The cutting blade 56 is now supporting the blade handle 24 by itself. The blade handle 24 may then be moved relative to the cutting blade 56 so as to increase the spacing between the microkeratome registration surface 28 of the blade handle 24 and the cutting edge 80 of the cutting blade 56, or stated another way so as to increase the spacing "S" between the registrant 32 of the blade handle 24 and the front wall 92 of its corresponding registration cavity 84 on the blade 56. Preferably, the bottom surface 48 of the blade handle 24 is maintained in interfacing relation with the top surface 60 of the cutting blade 56 during this movement. Stated another way, the noted relative movement between the blade handle 24 and cutting blade 56 is in a direction that is at least generally parallel with the top surface 60 of the cutting blade 56 and the bottom surface 48 of the blade handle 24. The blade handle 24 is moved relative to the cutting blade 56 in this manner until each registrant 32 cooperates with its corresponding registration surface 94, more typically a portion thereof. This then registers or aligns the cutting edge 80 of the cutting blade 56 relative to the microkeratome registration surface 28 of the blade handle 24, which in turn registers or aligns the cutting edge 80 of the cutting blade 56 in a desired position within the microkeratome 4. In one embodiment, each registrant 32 is separated from its corresponding front wall 92 by a distance of at least about 1 millimeter when the registrant 32 is interfacing with its corresponding registration surface 94.

The blade handle 24 is fixed to the cutting blade 56 when in the above-noted registered position. This emphasizes the desirability of using a light curable epoxy, including a UV curable epoxy. That is, a light curable epoxy allows the blade handle 24 to be mounted on the blade 56 in the above-noted manner so as to register the position of the blade handle 24 relative to the cutting blade 56 before the light curable epoxy sets. An appropriate light source (e.g., UV) may then be directed at the light curable epoxy to cure the same (in less than 10 seconds in the case of at least certain UV curable epoxies) and thereby fix the position of the blade holder 24 relative to the cutting blade 56. Having the position of the cutting edge 80 of the blade 56 registered relative to the microkeratome registration surface 28 of the blade handle 24 registers the position of the cutting edge 80 when installed in the microkeratome 4. Once again, the microkeratome registration surface 28 of the blade handle 24 is registered or aligned relative to the cutting tool registration surface 14 of the head assembly 10 of the microkeratome 4.

Figure 8B:
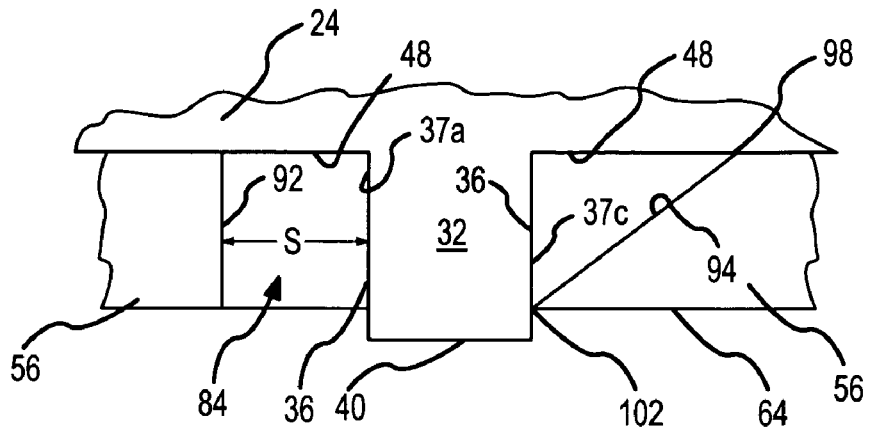
FIG. 8B is a cutaway, side view illustrating a registrant of a blade handle of the cutting tool utilized by the microkeratome of FIG. 1, while engaging a registration surface of the cutting blade.
Figure 8C:
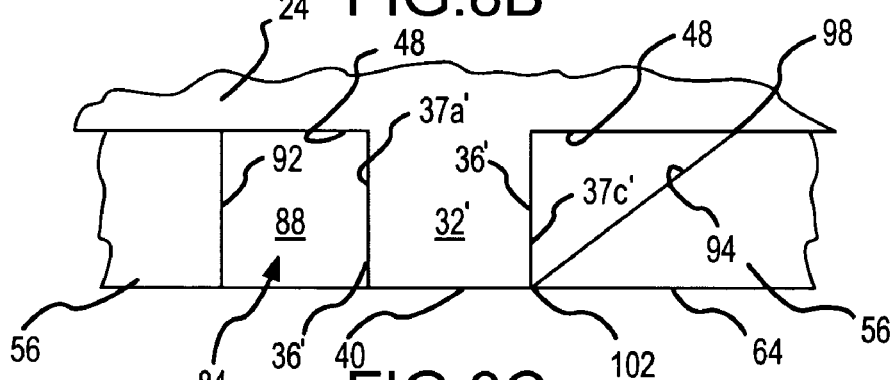
FIG. 8C is a cutaway, side view illustrating an alternative embodiment of a registrant of the blade handle of the cutting tool utilized by the microkeratome of FIG. 1, while engaging the registration surface of the cutting blade.
Figure 8D:
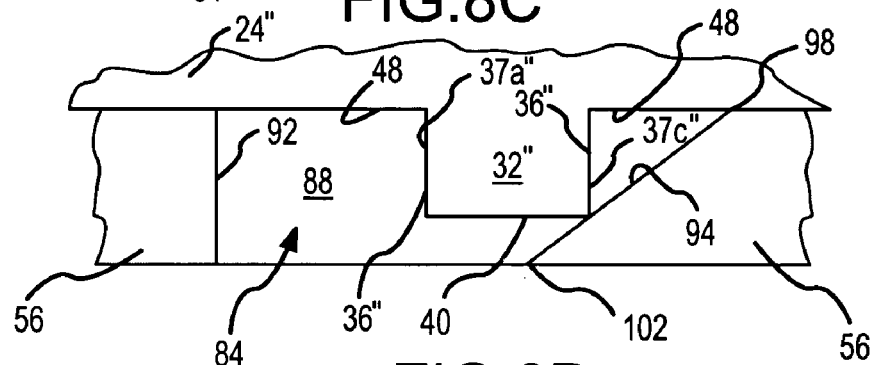
FIG. 8D is a cutaway, side view illustrating yet another alternative embodiment of a registrant of the blade handle of the cutting tool utilized by the microkeratome of FIG. 1, while engaging the registration surface of the cutting blade.
Figure 8A:
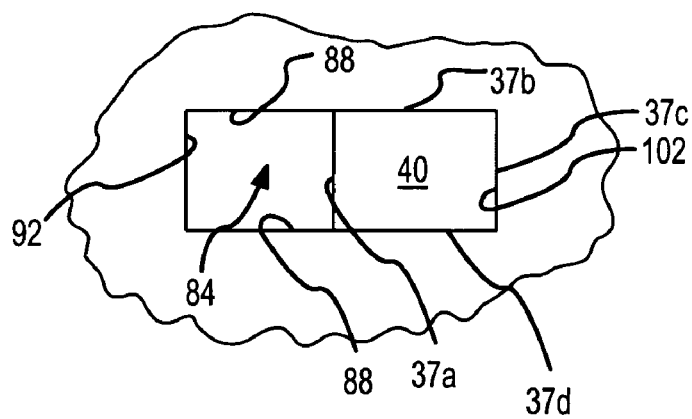
FIG. 8A is a cutaway, bottom view illustrating one registrant of the blade handle of the cutting tool utilized by the microkeratome of FIG. 1, while engaging a registration surface of the cutting blade.

Any appropriate cooperation between a given registrant 32 of the blade handle 24 and its corresponding registration surface 94 of the cutting blade 56 may be utilized that provides the desired registration or alignment of the cutting edge 80 of the cutting blade 56 relative to the microkeratome registration surface 28 of the blade handle 24 in the longitudinal or fore-aft dimension. In one embodiment, the contact between a registrant 32 and its corresponding registration surface 94 is limited to being at least generally along a line. Stated another way, the interface between a given registrant 32 and its corresponding registration surface 94 is limited to a "line contact" in one embodiment. This may be provided in any number of manners. Three options are illustrated in FIGS. 8B–D. FIG. 8B illustrates that the registrant 32 actually extends below the bottom surface 64 of the cutting blade 56, such that the lower edge 102 of the registration surface 94 engages a portion of the peripheral wall 36 of the registrant 32, namely the side wall 37c. FIG. 8C illustrates that the lower edge 102 of the registration surface 94 engages a registrant 32' of the blade handle 24' at least generally at the intersection between the peripheral wall 36 and the bottom wall 40 of the registrant 32. FIG. 8D illustrates that the intersection between the peripheral wall 36 and the bottom wall 40 of the registrant 32 engages its corresponding registration surface 94 somewhere between the lower edge 102 of the registration surface 94 and the upper edge 98 of this registration surface 94. Preferably, the registrant 32 interfaces with its corresponding registration surface 94 closer to the lower edge 102 than its upper edge 98, and including at the intersection between the bottom surface 64 of the blade 56 and the corresponding registration surface 94.

Standard semiconductor processing techniques may be utilized to fabricate the cutting blade 56 of the cutting tool 20. One significant advantage of using this technique is the accuracy with which the cutting blade 56 may be fabricated, particularly the accuracy of the position of the cutting edge 80 relative to the position of the registration surface 94 of each registration cavity 84 of the cutting blade 56. FIGS. 9A–D illustrate a number of steps in one method by which the cutting blade 56 may be fabricated using standard semiconductor processing techniques. Initially, a suitable material is selected for the fabrication of the cutting blade 56. Suitable materials for fabrication of the cutting blade 56 using the process described herein include without limitation single crystal silicon, single crystal quartz, and potentially other single crystal material having suitable crystal-plane selective etchants. Those materials that are suitable for fabrication of the cutting blade 56 generally are those that may be etched so that the etch will stop at a predetermined place/position within the material (e.g., at a particular crystal plane within the same material, that in effect acts as an etch stop), and further where the same etch behavior exists regardless of the location of the opening in the mask being utilized for the etch. Regarding the latter characterization, the material must be such that a particular etchant will behave the same anywhere within the material that is to be etched. It is really the combination of the material and the selected etchant that allows the etchant to anisotropically etch the material in the desired manner to define the cutting blade 56.

Figure 9A:
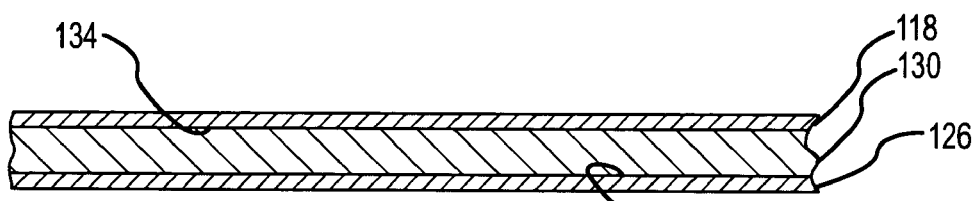
FIG. 9A is a cross-sectional view of a pair of masking layers formed on opposing surfaces of a substrate or wafer.

The material from which the cutting blade 56 is fabricated in accordance with FIGS. 9A–D generally may be characterized as a substrate 130, and will more typically be in the form of a wafer 130. It should be appreciated that wafers that are "commonly available" for the fabrication of semiconductor devices (e.g., silicon wafers having top and bottom surfaces parallel with either the (110) and (100) crystal planes) may not be suitable in relation to defining the desired blade angle θ for one or more applications of the cutting blade 56. In any case, masking layers 118, 126 are defined on an upper surface 134 and a lower surface 138, respectively, of the wafer 130 using conventional semiconductor processing techniques. This is illustrated in FIG. 9A. The masking layers 118, 126 may be formed on the corresponding surface 134, 138 of the wafer 130 in any appropriate manner (e.g., chemical vapor deposition, physical vapor deposition, or thermal growth in the case of silicon dioxide on silicon). Any material that may be patterned for a subsequent selective etching of the wafer 130 may be utilized by the masking layers 118, 126 (e.g., silicon nitride, silicon oxide).

Figure 9B:
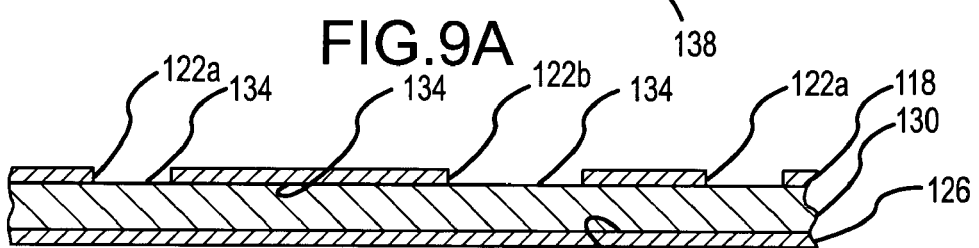
FIG. 9B is a cross-sectional view after a cutting blade mask has been transferred onto one of the masking layers of FIG. 9A, along with the resulting openings in the masking layer.
Figure 9C:
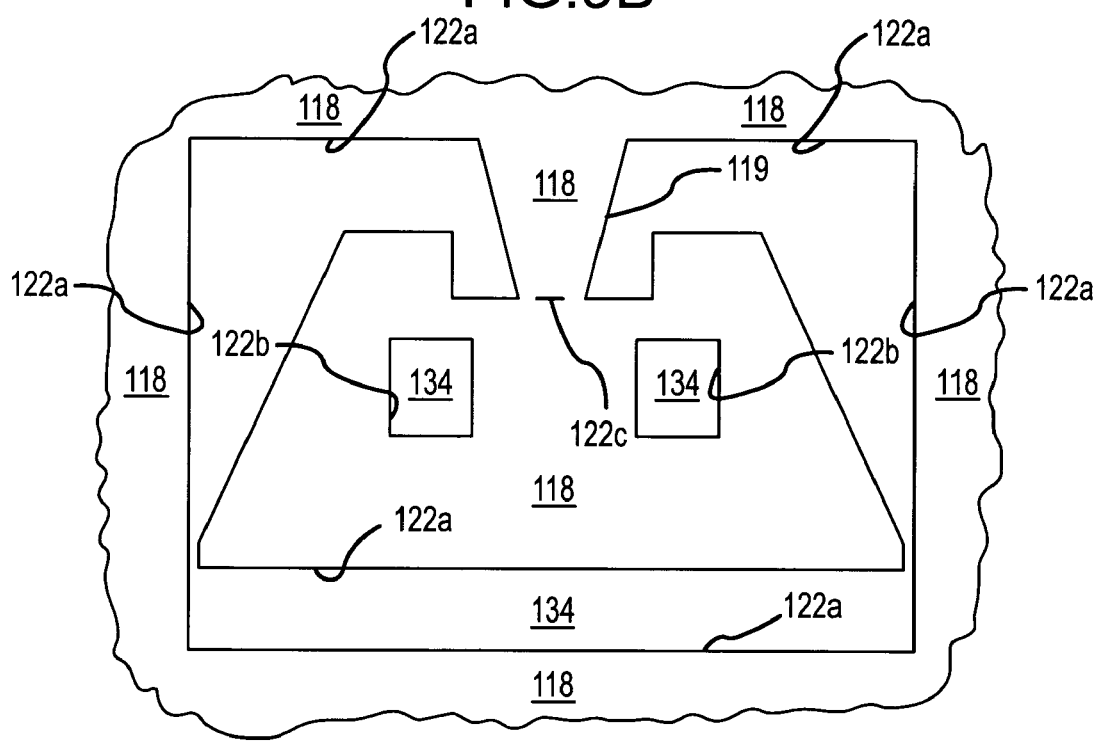
FIG. 9C is a top plan view of the openings in the masking layer illustrated in FIG. 9B
Figure 9D:
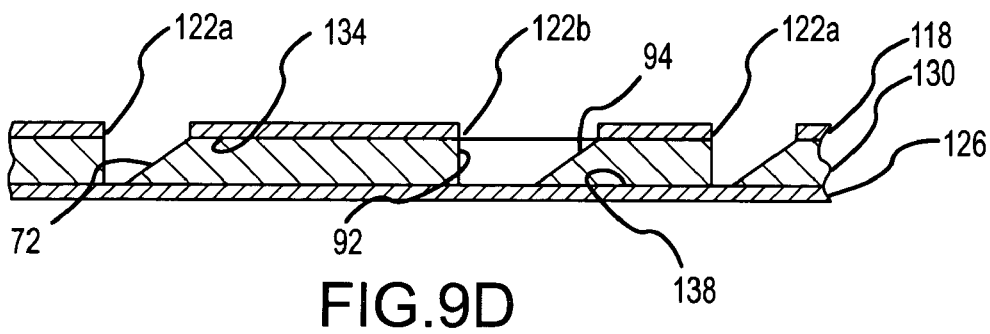
FIG. 9D is a cross-sectional view after the substrate/wafer has been etched to define the cutting blade of the cutting tool utilized by the microkeratome of FIG. 1.

What may be characterized as a blade mask is transferred onto the upper masking layer 118 in a manner known in the art for purposes of defining the cutting blade 56 and as illustrated in FIGS. 9B–C. Multiple masking layer openings or apertures 122a–c are formed on the upper masking layer 118 to define each cutting blade 56 that is to be fabricated from the wafer 130. These masking layer apertures 122a–c extend entirely through the upper masking layer 118 to expose desired, selective portions of the upper surface 134 of the wafer 130. Any appropriate technique may be utilized for transferring the blade mask onto the upper masking layer 118, including photomasking, masking, photolithography, microlithography, which is then followed by a suitable technique of etching the pattern into the upper masking layer 118 by means of wet chemical etching, plasma etching, reactive ion etching, or ion beam milling. The creation of the hard mask can also be accomplished using a dual step process of using the photoresist to define the pattern into an intermediate layer of silicon dioxide. Once the photoresist is stripped, the silicon dioxide is then used as an etch mask layer to define the silicon nitride by means of hot phosphoric acid.

The masking layer aperture 122a is sized and configured to define the first cutting edge surface 72 of the cutting blade 56 and the perimeter of the cutting blade 56 (the cutting edge 80, side surfaces 68, and rear surface 106). Each masking layer aperture 122b is "interiorly" disposed (inwardly of what will ultimately be the perimeter of the cutting blade 56) and is sized and configured to define a registration cavity 84 for the cutting blade 56. A masking layer aperture 122c is also formed through the upper masking layer 118 to define a score or score line within the wafer 130 to facilitate the removal of the cutting blade 56 from the wafer 130 after the blade 56 has been fabricated by an anisotropic etch (identified by reference numeral 132 in FIGS. 12 and 13A). This score need not, but may, pass through the entire vertical extent of the wafer 130.

No portion of the lower surface 138 of the wafer 130 needs to be patterned to fabricate the cutting blade 56 from the wafer 130. As such, no portion of the lower surface 138 needs to be exposed to an etchant for the fabrication of the cutting blade 56. However, a masking layer opening or aperture would be formed in the lower masking layer 126 in order to define the second cutting edge surface 66' of the cutting blade 56' of FIG. 3B.

After the upper masking layer 118 (and lower masking layer 126 if required by the desired cutting edge configuration) has been processed to define the desired configuration for the cutting blade 56 and the various individual surfaces thereof, the wafer 130 is exposed to a suitable etchant. One way to execute the desired etching operation is to dispose the wafer 130 in an etchant bath. In any case, those portions of the upper surface 134 of the wafer 130 that are exposed to the etchant will have material removed to define the configuration illustrated in FIG. 9D, which corresponds with the cutting blade 56. The etchant simultaneously defines the first cutting edge surface 72 and the registration surface 94 of each registration cavity 84 utilized by the blade 56, and also defines the perimeter of the cutting blade 56. A small portion of the cutting blade 56 remains attached to the wafer 130 in the form of a blade support tab at this time (see FIG. 12 to be discussed below, where this blade support tab is identified by reference numeral 131). This blade support tab is disposed under the portion of the upper mask 118 identified by reference numeral 119 in FIG. 9C. The etchant also etches are least partially through the wafer 130 through the mask aperture 122c to define a score (see FIG. 12 to be discussed below, where this score is identified by reference numeral 132). Generally, the cutting blade 56 is thereafter separated from the remainder of the wafer 130 by fracturing or breaking the wafer 130 along this score.

As noted above, an anisotropic etchant is utilized to fabricate the cutting blade 56. The anisotropic etchant simultaneously forms the first cutting edge surface 72 and the registration surface 94 of each registration cavity 84 as planar, parallel surfaces. This is done by selecting an anisotropic etchant that will in effect stop etching when reaching a certain crystal plane that defines the desired orientation for the first cutting edge surface 72 relative to the top surface 60 of the cutting blade 56. Generally, the material defining the wafer 130 and the selected etchant must be such that the behavior of the etchant is the same, regardless of the location of any mask aperture in the upper masking layer 118 (or the lower masking layer 126 for that matter). For the case of the wafer 130 being single crystal silicon and the first cutting edge surface 72 and the registration surface 94 of each registration cavity 84 being parallel with a {111} crystal plane, an appropriate anisotropic etchant for simultaneously defining the first cutting edge surface 72 and each registration surface 94 is KOH. That is, the KOH etchant will etch to, but not through, the first (111) crystal plane that is disposed under the edge of the upper masking layer 118 (corresponding with the upper edge 76 and the upper edge 98).

Fabricating the cutting blade 56 in the above-noted manner provides a number of advantages. Initially, the position of the cutting edge 80 relative to the position of each registration surface 94 can be done with a very high degree of accuracy due to the high degree of accuracy with which mask apertures can be formed in a mask in accordance with the foregoing. Moreover, the first cutting edge surface 72 is simultaneously formed with the registration surface 94 of each registration cavity 84, and this is done so that the cutting edge surface 72 and the registration surface 94 of each registration cavity 84 are disposed in parallel relation to a high degree of accuracy. As noted above, the anisotropic etch will proceed to the same exact crystal plane when defining each of the first cutting edge surface 72 and the registration surface 94 of each registration cavity 84. The etch will then have the same effect on both the first cutting edge surface 76 and the registration surface 94 of each registration cavity 84. Each of these factors contributes to being able to enhance the precision with which the cutting edge 80 of the blade 56 is disposed relative to a particular structure.

Figure 10:
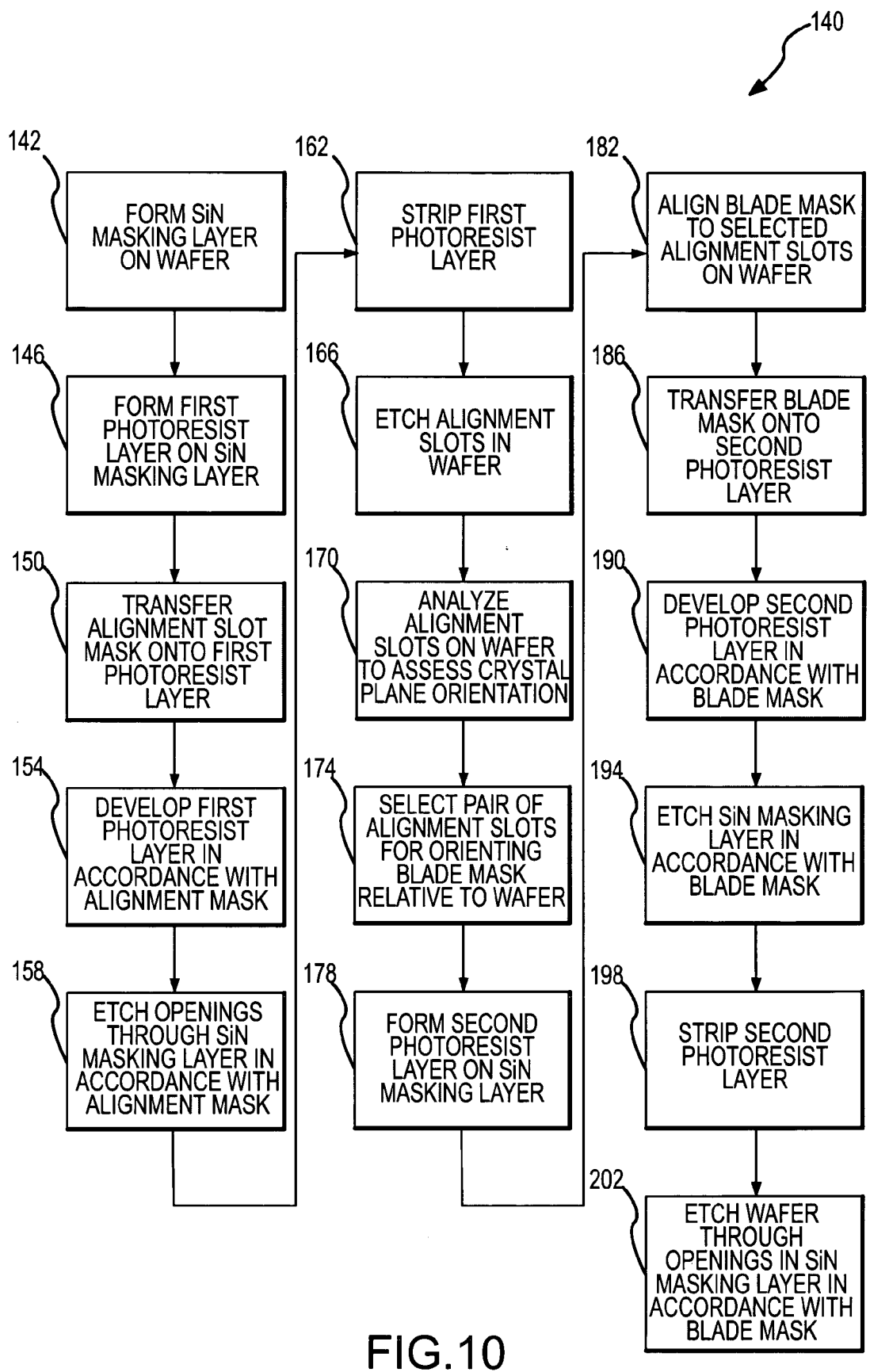
FIG. 10 is a flowchart illustrating one method of fabricating multiple blades from a wafer, including steps that correspond with FIGS. 9A–D.

FIG. 10 depicts one embodiment of a protocol 140 for fabricating one or more cutting blades 56 from the wafer 130. This protocol 140 utilizes the basic steps/results that are illustrated in FIGS. 9A–D. Step 142 of the protocol 140 is directed to forming a masking layer on a wafer (e.g., wafer 130). In the illustrated embodiment, what is commonly referred to in the art as a "hard mask" will ultimately be formed from this particular masking layer. Silicon nitride is used for the masking layer by step 142, although other materials may be appropriate. Any appropriate way of forming the silicon nitride masking layer on the wafer may be utilized by step 142.

A first photoresist layer is formed on the silicon nitride masking layer in accordance with step 146 of the protocol 140. Either a positive-acting or negative-acting photoresist material may be used by step 146. Any appropriate way of forming the first photoresist layer on the silicon nitride masking layer may be utilized by step 146. What may be characterized as an alignment slot mask is then transferred onto the first photoresist layer through execution of step 150. Generally, this alignment slot mask is used to define certain structures on the wafer to thereafter align what may be characterized as a "blade mask" to the wafer in a certain manner, more specifically to align the blade mask to a certain crystal orientation associated with the wafer. This "blade mask" is that which has a layout of masking layer openings extending therethrough such that selected portions of the wafer will be etched in a manner so as to simultaneously fabricate/define a plurality of cutting blades 56.

Step 154 of the protocol 140 indicates that the first photoresist layer is developed in accordance with the alignment slot mask to create a plurality of openings that extend completely through the first photoresist layer in a layout that will be discussed in more detail below in relation to FIG. 11. "Developing" the first photoresist layer includes both exposing portions of the first photoresist layer to an appropriate type of light (either that portion of the first photoresist material that is to be removed in the case of a positive-acting photoresist material, or that portion of the first photoresist layer that is to remain in the case of a negative-acting photoresist material), and thereafter exposing the "light treated" first photoresist layer to an appropriate developer to remove portions of the first photoresist layer in accordance with the alignment slot mask. Openings in accordance with the desired/required layout are formed through the entire vertical extent of the first photoresist layer to expose the underlying silicon nitride masking layer.

Appropriate openings are next etched through the entire vertical extent of the silicon nitride masking layer in accordance with step 158 of the protocol 140. The layout of these openings is in accordance with the openings in the first photoresist layer, and thereby in accordance with the alignment slot mask. In one embodiment, a reactive ion etch is used to define the openings in the silicon nitride masking layer in the layout required by the alignment slot mask. Other types of etches may be appropriate. In any case, this then exposes selected portions of the upper surface of the underlying wafer. The first photoresist layer is then stripped (step 162) from the now patterned silicon nitride masking layer, and another etch is initiated to form alignment slots that extend within, but typically not through, the wafer. In one embodiment, the etch from step 166 of the protocol 140 is a KOH etch. Other etches may be appropriate. The etch from step 166 reaches the wafer through the openings in the silicon nitride masking layer associated with step 158 of the protocol 140, and thereby in accordance with the alignment slot mask of step 150.

The alignment slots on the wafer formed in accordance with steps 146–166 of the protocol 140 are analyzed to determine which alignment slot(s) is suitably aligned with a particular crystal orientation associated with the wafer. This is represented by step 170 of the protocol 140 of FIG. 10. The alignment slot(s) that are aligned with a particular crystal orientation associated with the wafer are then identified (step 174 of the protocol 140) for subsequent use in aligning/orienting the blade mask to the wafer.

Figure 11:
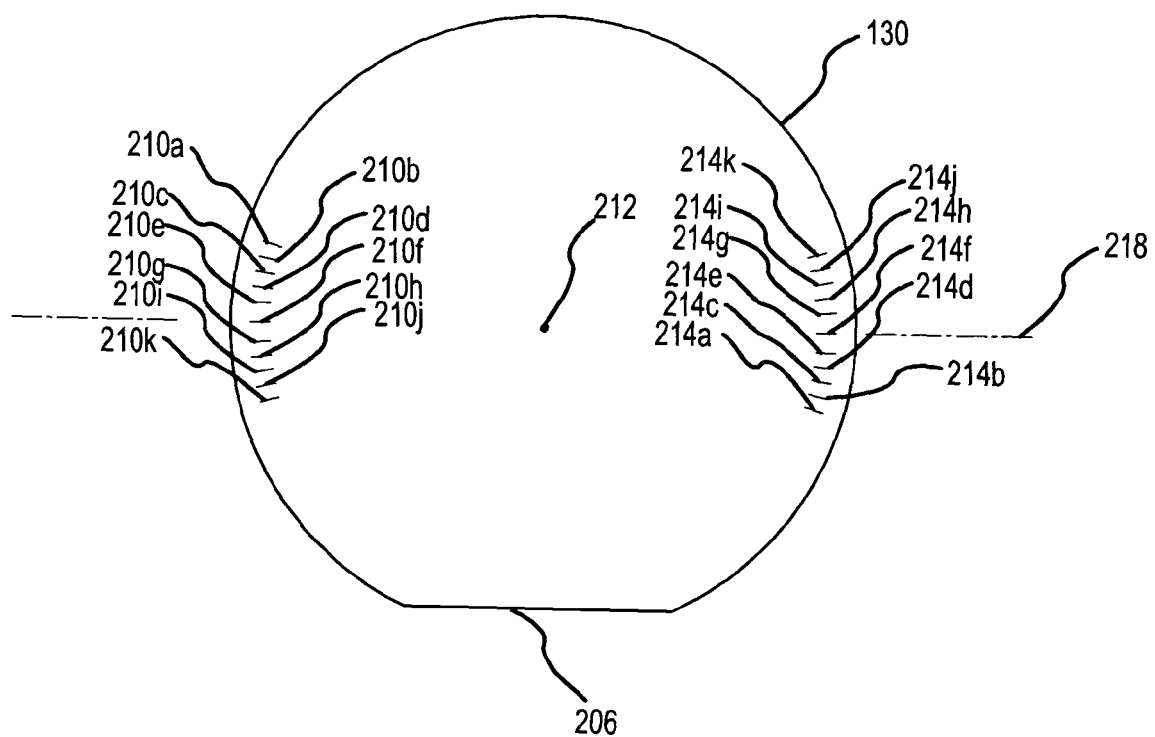
FIG. 11 is a plan view of a wafer with alignment slots etched therein for aligning a blade mask relative to the wafer.

FIG. 11 illustrates one way in which the alignment slots referred to by the protocol 140 of FIG. 10 may be formed on the wafer 130 to orient the blade mask relative to the wafer 130. The wafer 130 includes a flat 206 that is disposed at the 6:00 o'clock position. A reference axis 218 extends from the 3:00 o'clock position to the 9:00 o'clock position, through a center 212 of the wafer 130. Generally, a plurality of alignment slots 210a–k are formed on one side of the wafer 130, while a plurality of alignment slots 214a–k are formed on an opposite side of the wafer 130. Any number of alignment slots 210a–k, 214a–k may be utilized. The alignment slot 210a corresponds with the alignment slot 214a, the alignment slot 210b corresponds with the alignment slot 214b, and so forth. Corresponding alignment slots 210a–k/214a–k are disposed along a common axis that extends through the center 212 of the wafer 130. That is, the alignment slots 210a, 214a are positioned along a common axis that extends through the center 212 of the wafer 130, the alignment slots 210b, 214b are positioned along a common axis that extends through the center 212 of the wafer 130, and so forth. The axes along which corresponding slots 210a–k, 214a–k are disposed are preferably equally spaced about the center 212 of the wafer 130. That is, the axis along which the alignment slots 210b, 214b are disposed is rotated counterclockwise a predetermined amount from the axis along which the slots 210a, 214a are disposed, the axis along which the alignment slots 210c, 214c are disposed is rotated counterclockwise this same predetermined amount from the axis along which the slots 210b, 212b are disposed, and so forth.

The alignment slots 210a–k, the alignment slots 214a–k, or both may be analyzed to identify which corresponding pair of alignment slots (e.g., (210a, 214a); (210b, 214b); (210c ; 214c), etc) may be used to align the blade mask to the wafer 130 for purposes of step 182 of the protocol 140 of FIG. 10. This analysis may be done in any appropriate manner, including optically. This analysis is undertaken pursuant to step 170 of the protocol 140 of FIG. 10 that was discussed above. Generally, the alignment slot 210a–k that is narrowest or of the smallest width ("width" being the dimension that is perpendicular to its length dimension, which is along a radius extending from the center 212 of the wafer 130) is that which is most closely aligned with a predetermined crystal plane of the wafer. The same is true for the alignment slots 214a–k.

Once a corresponding pair of alignment slots 210, 214 has been identified as being suitably aligned with a predetermined crystal plane of the wafer (if one alignment slot 210 is identified, its corresponding alignment slot 214 will also be of the narrowest width from the group of alignment slots 214a–k, and vice versa), this pair of alignment slots 210, 214 is "selected" as noted by step 174 of the protocol 140 of FIG. 10. That is, the location of this particular pair of alignment slots 210, 214 is noted such that alignment marks on the blade mask may be aligned thereto in accordance with step 182 of the protocol 140. More specifically, a second photoresist layer is formed on the silicon nitride masking layer in accordance with step 178 of the protocol 140 and in any appropriate manner. Either a positive-acting or negative-acting photoresist again began may be utilized. In any case, the blade mask is aligned with the selected alignment slots in accordance with step 182 of the protocol 140, and the blade mask is thereafter transferred onto the second photoresist layer in accordance with step 186. The blade mask is such that the alignment slots 210a–k, 214a–k will not interfere with the fabrication of the individual cutting blades 56 (e.g., the alignment slots 210a–k, 214a–k are disposed beyond the region of the wafer on which cutting blades 56 are fabricated).

Step 190 of the protocol 140 indicates that the second photoresist layer is developed in accordance with the blade mask to create openings that extend completely through the second photoresist layer. "Developing" the second photoresist layer includes both exposing portions of the second photoresist layer to an appropriate type of light (either that portion of the second photoresist material that is to be removed in the case of a positive-acting photoresist material, or that portion of the second photoresist layer that is to remain in the case of a negative-acting photoresist material), and thereafter exposing the "light treated" second photoresist layer to an appropriate developer to remove the desired portions of the second photoresist layer. Openings in accordance with the desired/required layout are formed through the entire vertical extent of the second photoresist layer to expose the underlying silicon nitride masking layer.

Appropriate openings in accordance with the blade pattern are next etched through the entire vertical extent of the silicon nitride masking layer pursuant to step 194 of the protocol 140. The layout of these openings is in accordance with the openings in the second photoresist layer, and thereby in accordance with the blade mask. In one embodiment, a reactive ion etch is used to define these openings in the silicon nitride masking layer required by the blade mask. Other types of etches may be appropriate. In any case, this then exposes selected portions of the upper surface of the underlying wafer. The second photoresist layer is then stripped (step 198) from the now patterned silicon nitride masking layer, and another etch is initiated through step 202 of the protocol 140. This particular etch defines the various blades 56 that are included in the blade mask associated with step 186 of the protocol 140, and the result of which corresponds with FIG. 9D. In one embodiment, the etch of step 202 is a KOH etch. Other etches may be appropriate.

Any number of blades 56 may be simultaneously fabricated in accordance with the protocol 140 of FIG. 10, depending of course on the size of the blades 56 and the size of the wafer 130 from which the blades 56 are fabricated. One blade pattern that may be utilized by the protocol 140 results in the layout illustrated in FIG. 12. Here, a number of rows and columns of blades 56 have been fabricated on the wafer 130 utilizing the protocol 140 of FIG. 10. Each blade 56 remains attached to the wafer 130 by a blade support tab 131 of the wafer 130 at this point in time. This is the only "interconnection" between each blade 56 and the wafer 130 at this time, and which is the result of the etch of step 202 of the protocol 140. All portions of the wafer 130 other than the blades 56 and their corresponding blade support tabs 131 may be characterized as a frame or skeleton 128 of the wafer 130 (e.g., a remainder). As such, a blade 56 may be characterized as being attached to its blade support tab 131, that in turn is attached to the frame 128.

Figure 12:
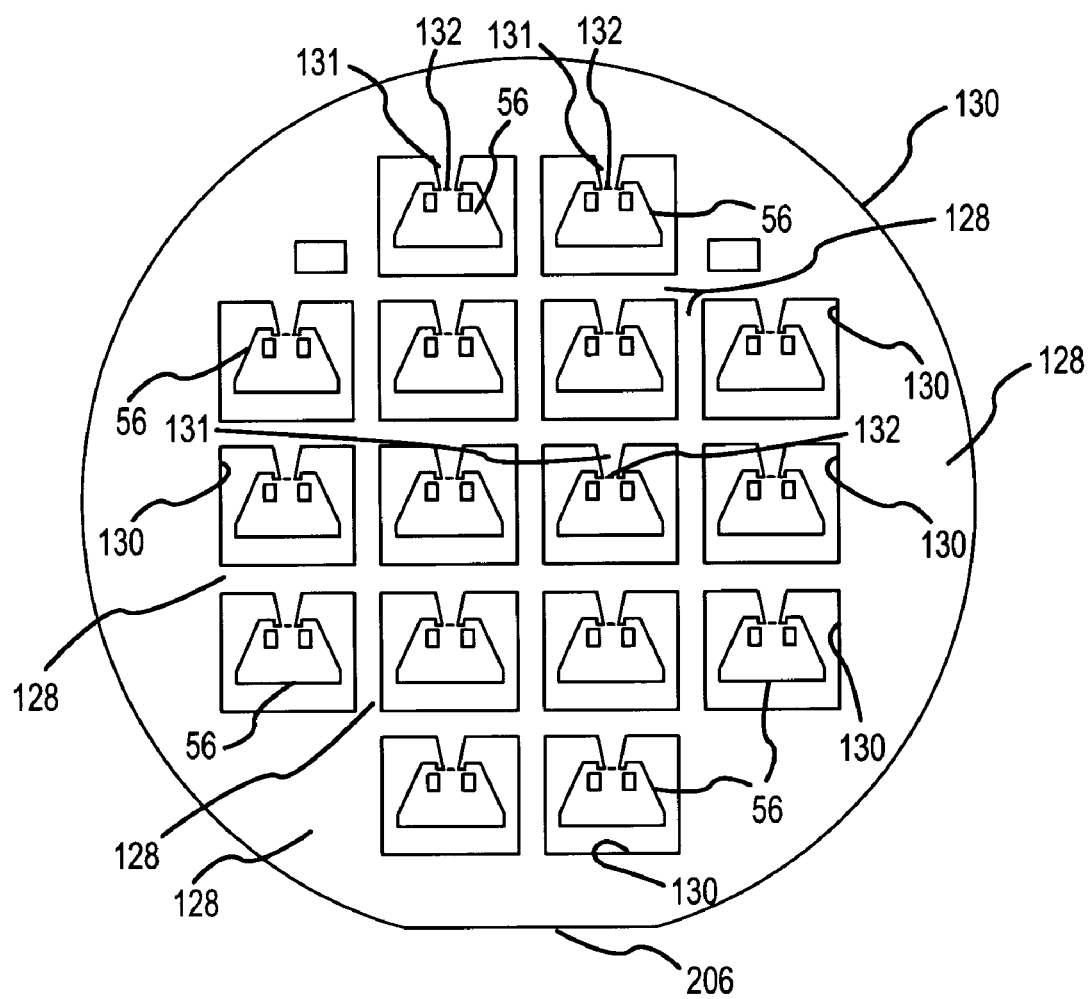
FIG. 12 is a plan view of a wafer having a plurality of cutting blades fabricated therefrom in accordance with the protocol of FIG. 10.
Figure 13A:
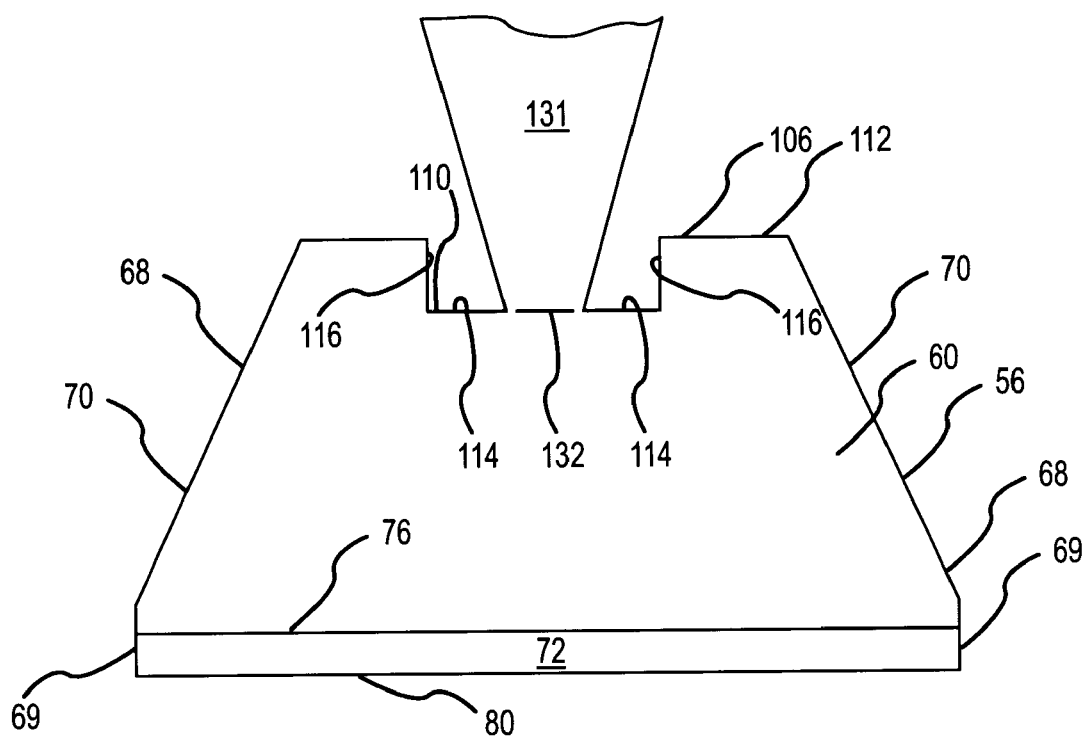
FIG. 13A is an enlarged, plan view of the interconnection between a single cutting blade and the wafer from FIG. 12.
Figure 13B:
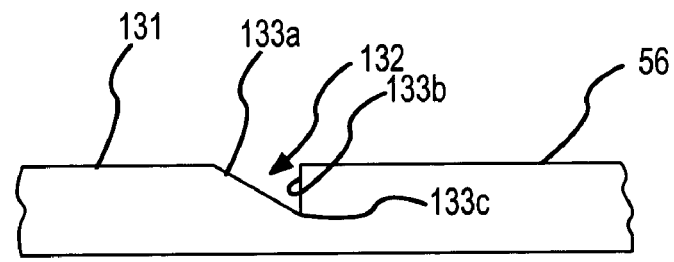
FIG. 13B is an enlarged, cutaway view of one embodiment of a blade separation score that is only schematically illustrated in FIG. 13A and which is used to separate the cutting blade from a corresponding blade support tab of the wafer.

Referring now to FIGS. 12 and 13A–B and as previously noted, a score 132 is formed on each blade support tab 131 to facilitate the removal of the corresponding blade 56 from the remainder of the wafer 130 in a manner that will be discussed in more detail below. Each score 132 may, but preferably does not, extend through the entire vertical extent of the wafer 130. In one embodiment, the depth of each score 132 is within a range of about 2% to about 75% of the thickness of the wafer 130. In another embodiment, the depth of each score 132 is on the order of about 10–30 microns, where the thickness of the wafer 130 is about 240 microns.

A pair of planar score surfaces 133a, 133b intersect at a location identified by reference numeral 133c in FIG. 13B (hereafter "intersection 133") to define the corresponding score 132 in the illustrated embodiment (e.g., a V-shaped configuration). The planar score surfaces 133a, 133b may each be disposed in any appropriate angular orientation. In the illustrated embodiment, the planar score surface 133a is parallel with the cutting edge surface 72, while the planar score surface 133b is perpendicular to the top surface 60 and bottom surface 64 of the blade 56. Other configurations may be appropriate for the score 132 and yet still facilitate separation of the cutting blade 56 from the wafer 130 in a desired manner.

It should be noted that the score 132 associated with each blade 56 preferably does not extend across the entire lateral extent of its corresponding blade support tab 131. That is, each score 132 preferably does not extend up to and intersect with that portion of the second section 114 of the notch 110 that is defined by the etch associated with step 202 of the fabrication protocol 140 of FIG. 10. One benefit of this preferred configuration is that it enhances the structural integrity of the blade support tabs 131. Stated another way, having each score 132 extend all the way across its corresponding blade support tab 131 could possibly weaken the interconnection between the blade support tab 131 and its corresponding blade 56. That is, in a situation where the score 132 did extend across the entire lateral extent of the blade support tab 131 (not shown), the etch associated with step 202 of the fabrication protocol 140 of FIG. 10 may further reduce the lateral extent of that end of the blade support tab 131 that interfaces with its corresponding blade 56. This could weaken the "joint" between the blade support tab 131 and its corresponding blade 56 to the point of being susceptible to premature separation of the corresponding cutting blade 56 from the remainder of the wafer 130. The depth of the score 132 may also of course have an effect on the structural integrity of the blade support tab 131, or stated another way on the ability for the blade 56 to remain attached to the wafer 130, including while mounting a blade handle 24 thereon. In one embodiment, a portion of the blade support tab 131 is disposed beyond each end of the score 132 such that the score 132 does not extend across the entire width or lateral extent of the blade support tab 131, and the score 132 is about 2%–5% of the thickness of the blade 56. This provides sufficient structural integrity for the blade 56 to remain attached to the wafer 130 during handling and while mounting the handle 24 on the blade 56, and yet still facilitates separation of the blade 56 from the wafer 130 at least substantially along the score 132 at the desired time.

There are a number of other characteristics of note in relation to the scores 132. Initially, each score 132 is preferably aligned with a crystallographic plane such that the separation of the blades 56 occurs at least substantially along a crystallographic plane, and in one embodiment the intersection 133c of the planar score surfaces 133a, 133b of a given score 132 is aligned with a crystallographic plane. Moreover, preferably each score 132 is parallel with its corresponding cutting edge 80. Another is that the scores 132 are longitudinally offset from their corresponding first sections 112 of the rear surface 106 of the corresponding blade 56. That is, the scores 132 are "longitudinally recessed" relative to the rear edge of the corresponding cutting blade 56. Other configurations of the rear surface 106 of the blade 56 may be utilized and still provide this "longitudinally recessed" feature. That is, what is of importance is that the score 132 be positioned at a location that is longitudinally recessed from a most rearwardly disposed portion of the rear surface 106 of the blade 56. Stated another way, the score 132 is preferably disposed closer to the cutting edge 80 than the most rearwardly disposed portion of the rear surface 106 of the blade 56 (both measured along/parallel to the central, longitudinal reference axis 58 associated with the blade 56). This may be of benefit if one or more sharp edges develops during the separation of the blade 56 from the wafer 130 at least generally along its corresponding score 132.

Figure 13C:
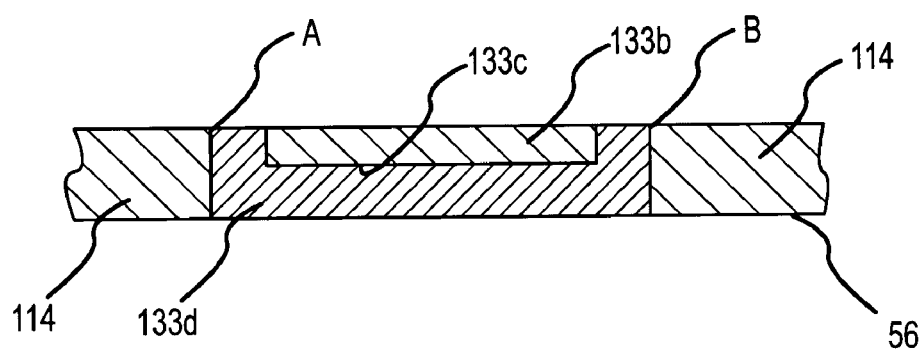
FIG. 13C is an enlarged, plan view of a portion of the rear of the cutting blade of FIG. 13A after its separation from the wafer along the score of FIG. 13B.

Separation of the cutting blade 56 from the remainder of the wafer 130 utilizing the score 132 produces the configuration that is illustrated in FIG. 13C. Locations A and B correspond with the locations where the blade support tab 131 had previously merged with the cutting blade 56. It can be seen that the planar score surface 133b of the score 132 has become part of the cutting blade 56. This also illustrates the preferred approach where the score 132 and the portion of the second section 114 of the notch 110 on the opposite sides thereof are both defined by an etch, and thereby are similarly shaded. In contrast, the region that is bounded by the pair of dashed lines, and further that does not include planar score surface 133b, is defined by fracturing the wafer 130. Reference numeral 133d identifies this fracture region and utilizes a different shading than the surfaces defining the planar score surface 133b and the second section 114. The fracture region 133d is longitudinally spaced from the rear-most portion of the cutting blade 56. In one embodiment, the fracture region 133d is coplanar with the second section 114, and may be considered as part thereof. In another embodiment, the fracture region 133d is parallel to, but longitudinally offset from, the second section 114 of the blade 56 (not illustrated). In this latter instance, the fracture regions 133d desirably still does not define the most rearwardly disposed portion of the cutting blade 56.

Figure 13D:
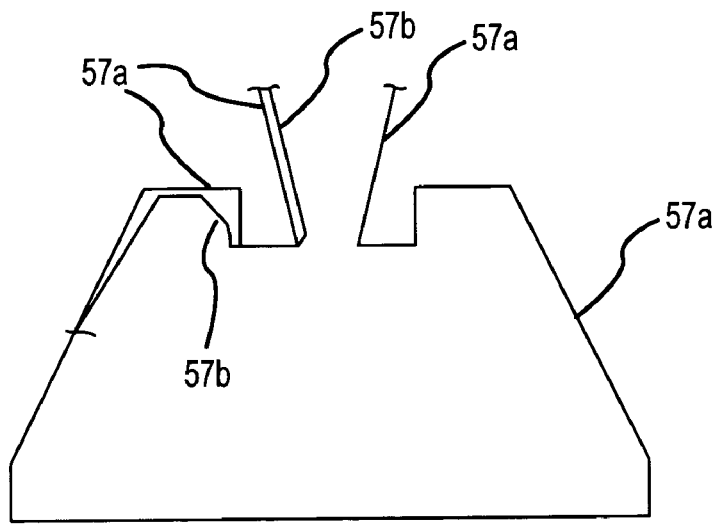
FIG. 13D is a plan view of a blade mask perimeter profile and one embodiment of an actual perimeter profile produced when anisotropically etching a wafer based upon this blade mask perimeter profile.

As noted above, there may be some variation between the blade mask and the resulting configuration of the blade 56 when etched from the wafer 130. For instance, FIG. 13D includes a reference numeral 57a that represents the blade mask perimeter profile for the blade 56. The entire blade mask perimeter profile 57a for a blade 56 is illustrated in FIG. 13D, as well as a portion of its corresponding blade support tab 131. Reference numeral 57b in FIG. 13D represents an actual perimeter profile of a blade 56 when fabricated from the wafer 130 by an anisotropic etch. That is, the actual perimeter profile 57b is that which is actually achieved when using an anisotropic etch from a blade mask have the blade mask perimeter profile 57a. Only a portion of the actual perimeter profile 57b is illustrated in FIG. 13D for convenience.

Blades 56 are separated from the remainder of the wafer 130 generally by first mounting a blade handle 24 on an individual cutting blade 56 in the above-noted manner so as to properly register the blade handle 24 to the cutting blade 56. Once the adhesive has cured an appropriate amount or once the blade handle 24 is otherwise sufficiently fixed to an individual blade 56, the blade handle 24 is moved (e.g., manually) relative to the wafer 130 so as to cause the wafer 130 to fracture along its corresponding score 132. In the illustrated embodiment, blade handles 24 are attached to each of the individual blades 56 on a wafer 130 while in a blade handle mounting fixture 224 (FIGS. 14–19). The wafer 130 with the blade handles 24 mounted on its various blades 56 is then transferred to a blade separation fixture 300 where the individual blades 56, with a blade handle 24 mounted thereon, are separated from the remainder of the wafer 130 (FIGS. 20–23).

FIGS. 14–19 illustrate a desirable configuration for allowing blade handles 24 to be mounted on individual cutting blades 56 while still attached to and thereby part of the wafer 130. A base plate 220 is appropriately attached to a bottom surface 278 of a blade handle mounting fixture 224. One or more appropriate fasteners (not shown) are directed through mounting holes 222 in the base plate 220 and into mounting holes 296 formed on the bottom surface 278 of the blade handle mounting fixture 224. Any appropriate way of interconnecting the base plate 220 with the blade handle mounting fixture 224 may be utilized.

Figure 17:
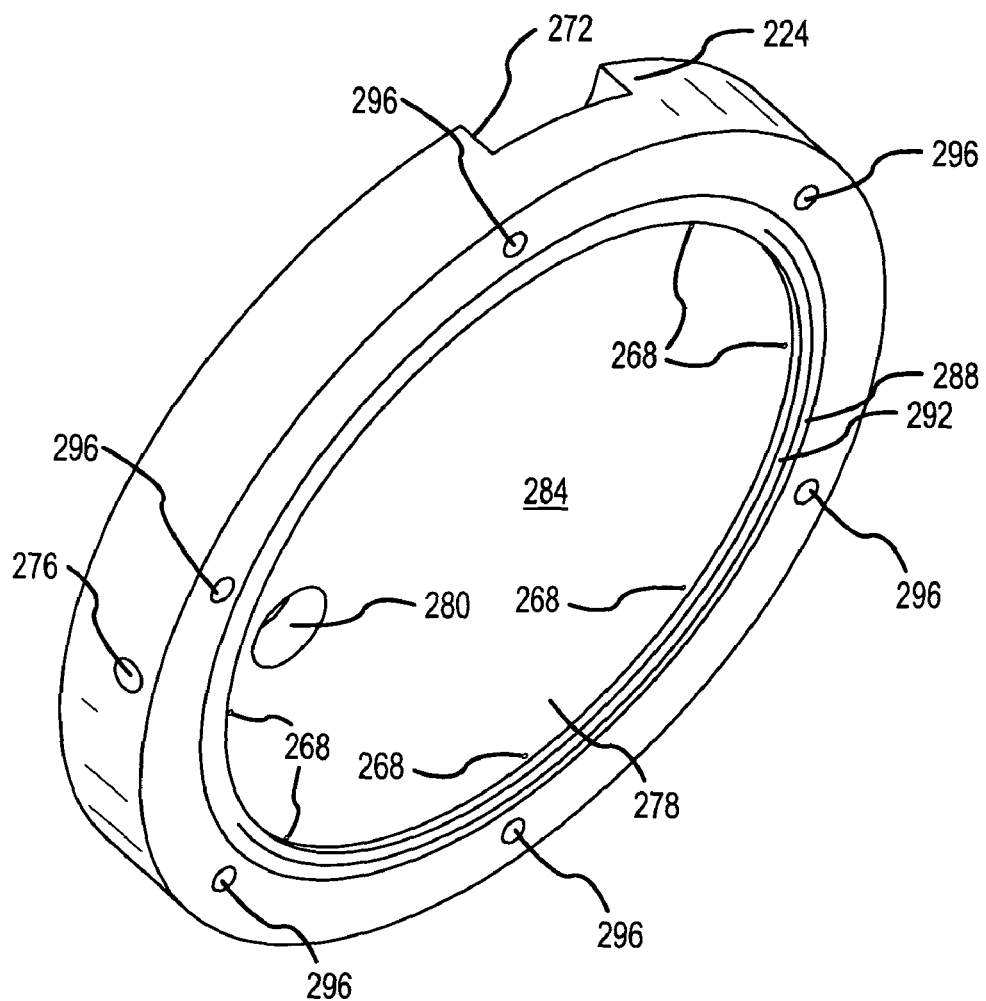
FIG. 17 is a perspective view of a lower surface of the blade handle mounting fixture of FIG. 14.
Figure 18:
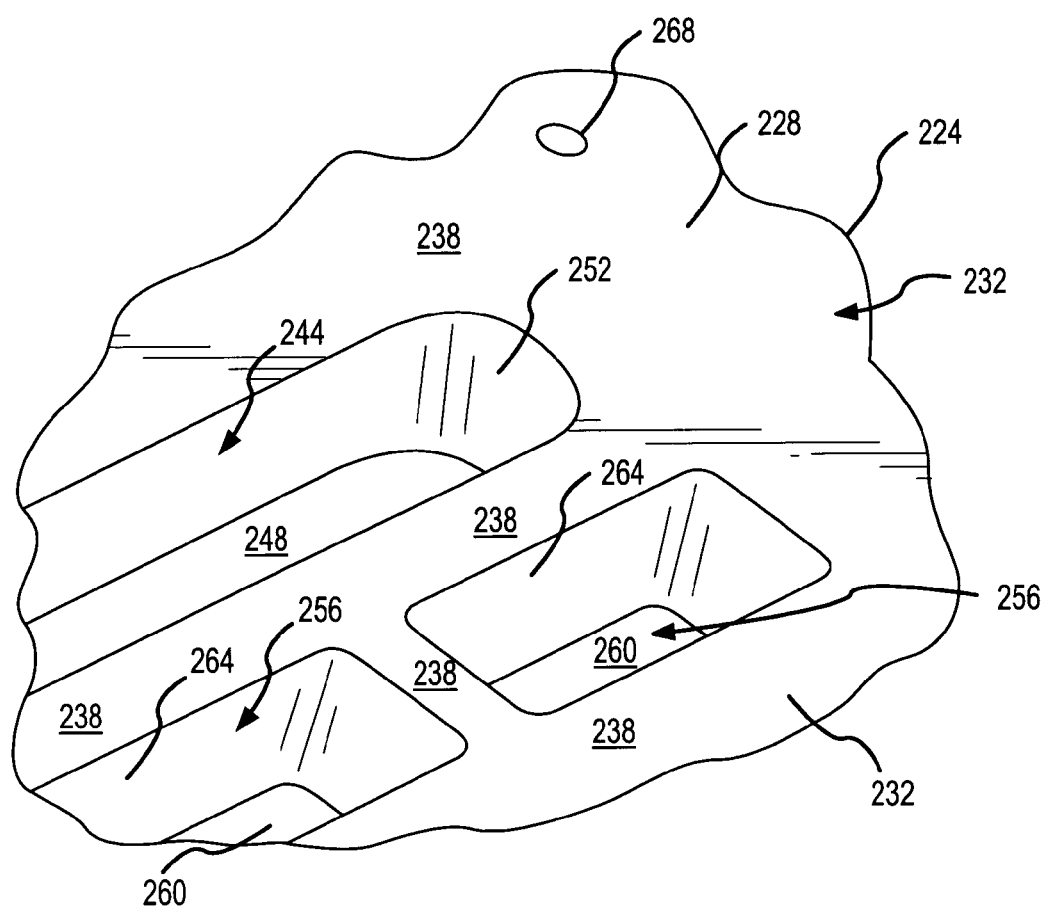
FIG. 18 is an enlarged, perspective view of a portion of the upper surface of the blade handle mounting fixture of FIG. 14 that would interface with one of the cutting blades.

The base plate 220 generally cooperates with the blade handle mounting fixture 224 to define a vacuum chamber 284 (FIG. 17). More specifically, an annular groove 288 is defined on the bottom surface 278 of the blade handle mounting fixture 224. An annular seal ring 292 is disposed within this annular groove 288 and seats against an annular portion of a inner surface 223 of the base plate 220 that projects toward or faces the bottom surface 278 of the blade handle mounting fixture 224. The perimeter of the vacuum chamber 284 thereby corresponds with the annular seal ring 292, while the top and bottom of the vacuum chamber 284 are defined by the bottom surface 278 of the blade handle mounting fixture 224 and the inner surface 223 of the base plate 220, respectively.

A vacuum is generated within the noted vacuum chamber 284 by fluidly interconnecting a vacuum pump or the like (not shown) to a vacuum pull-down port 276 associated with the blade handle mounting fixture 224. This vacuum pull-down port 276 extends within the body of the fixture 224 and intersects with a vacuum linking port 280. This vacuum linking port 280 is disposed inwardly of the annular seal ring 292 and intersects with the bottom surface 278 of the fixture 224 so as to be fluidly interconnected with the vacuum chamber 284. A plurality of vacuum holes 268 are also disposed inwardly of the annular seal ring 292 so as to interface with the vacuum chamber 284. These vacuum holes 268 extend from the bottom surface 278 of the blade handle mounting fixture 224 to an upper surface 228 of the fixture 224 on which the wafer 130 is disposed.

The upper surface 228 of the blade handle mounting fixture 224 is configured to suitably support the wafer 130 and maintain the same in a fixed position while installing the blade handles 24 on the individual blades 56 when still part of the wafer 130. Generally, less than the entirety of the lower surface 138 of the wafer 130 is in actual contact with the upper surface 228 of the fixture 224. Moreover, the upper surface 228 of the fixture 224 is configured so as to reduce the potential for damage to the cutting edge 80 of each blade 56 while mounting the blade handles 24 on the individual blades 56 the wafer 130. The upper surface 228 of the fixture 224 is also configured so as to allow the bottom surface 48 of each blade handle 24 to properly seat on the top surface 60 of its corresponding blade 56 (e.g., so as to be in interfacing relation, or at least in closely spaced and parallel relation). When adhesives are used, there will of course be a bond line between the blade handle 24 and the blade 56. Finally, the blade 56 itself is directly supported by the fixture 224 (in one embodiment in coplanar relation with non-blade portions of the wafer 130 and including at least part of the above-noted frame 128), preferably in a manner such that the net moment about the corresponding score 132 is zero (i.e., no torque) when mounting a blade handle 24 on the cutting blade 56.

The upper surface 228 of the blade handle mounting fixture 224 includes a recess 232 having a base 236 that is vertically offset from an annular perimeter portion 230 of the upper surface 228. This base 236 includes a planar wafer supporting surface 238, a plurality of cutting edge cavities 244, and a plurality of registrant cavities 256. An annular side wall 240 of the recess 232 extends from the lower elevation wafer supporting surface 238 of the base 236 of the recess 232 to the higher elevation annular perimeter portion 230 of the upper surface 228 of the fixture 224. This annular side wall 240 at least substantially approximates a perimeter of the wafer 130. Preferably, the annular side wall 240 and the perimeter of the wafer 130 are disposed in closely spaced relation (e.g., such that there is no more than about a 1 millimeter gap between any portion of the annular side wall 240 and a corresponding portion of the perimeter of the wafer 130).

At least one notch 272 is formed on the upper surface 228 of the blade handle mounting fixture 224. Each notch 272 has a base 274 that is vertically offset from the wafer supporting surface 238 of the base 236 of the recess 232. The base 274 of each notch 272 is disposed at a lower elevation than the wafer supporting surface 238 of the base 236 of the recess 232. There is thereby a space between the wafer 130 and the base 274 of each notch 272. This space facilitates installation of the wafer 130 within the recess 232 of the blade handle mounting fixture 224, as well as the removal of the wafer 130 from the blade handle mounting fixture 224. Both manual (e.g., human operator) and a machine(s) are contemplated for one or both of the installation and removal of the wafer 130 relative to the blade handle mounting fixture 224.

Figure 16:
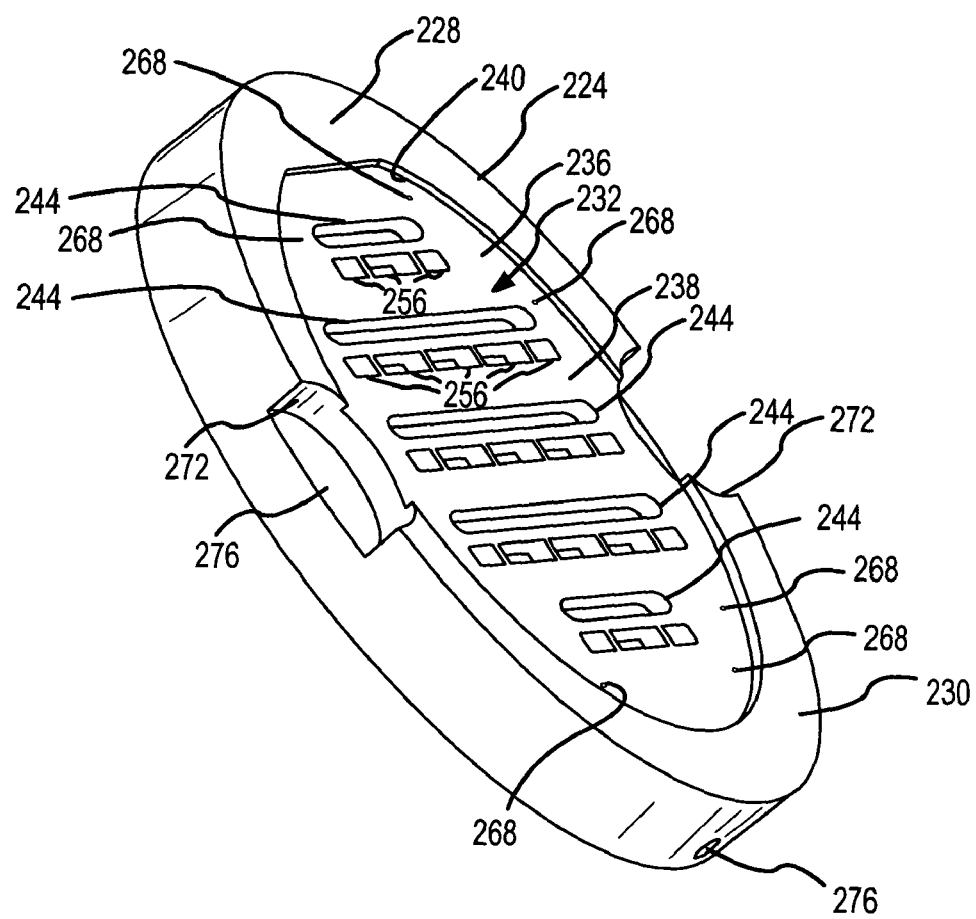
FIG. 16 is a perspective view of an upper surface of the blade handle mounting fixture of FIG. 14.

Multiple features are incorporated in the configuration of the base 236 of the recess 232 that is formed on the upper surface 228 of the blade handle mounting fixture 224 for receipt of the wafer 130. One is that the various vacuum holes 268 intersect with the base 236 of the recess 232. Preferably these vacuum holes 268 intersect with the wafer supporting surface 238 of the base 236 of the recess 232 (FIG. 16). The wafer supporting surface 238 interfaces with the lower surface 138 of the wafer 130 to vertically support the wafer 130 while on the fixture 224. When the wafer 130 is disposed within the recess 232, a vacuum is pulled through the various vacuum holes 268 against the overlying wafer 130, through the vacuum chamber 284, through the vacuum linking port 280, and through the vacuum pull-down port 276 by an appropriate source. Suction forces thereby retain the lower surface 138 of the wafer 130 against the planar wafer supporting surface 238 of the base 236 of the recess 232. Exactly how the suction or vacuum force is generated and transferred to the wafer 130 to retain the same against the fixture 224 is not of particular importance. Other configurations may be utilized to generate this type of retention force for the wafer 130 on the fixture 224.

Another feature of the base 236 of the recess 232 formed on the upper surface 228 of the blade handle mounting fixture 224 is that it includes multiple cutting edge cavities 244. Each cutting edge cavity 244 is defined by a base 248 that is vertically spaced from the wafer supporting surface 238, and a side wall 252 that extends from the lower elevation base 248 to the higher elevation wafer supporting surface 238 (e.g., FIG. 18). In the illustrated embodiment, at least part of the side wall 252 of each cutting edge cavity 244 is disposed in perpendicular relation to the adjacent portion of the wafer supporting surface 238 of the base 236 of the recess 232. Any appropriate orientation of the side wall 252 of the various cutting edge cavities 244 may be utilized.

What is of principal importance in relation to each cutting edge cavity 244 is that they be sized and oriented on the upper surface 228 of the fixture 224 such that the cutting edge 80 of each blade 56 will be disposed over one of the cutting edge cavities 244 when the wafer 130 is disposed within the recess 232 of the fixture 224. That is, the cutting edge 80 of each blade 56 is disposed in vertically spaced relation to the blade handle mounting fixture 224. Preferably, the cutting edge 80 of each blade 56 never contacts the fixture 224 while the wafer 130 is positioned thereon. In the illustrated embodiment, a given cutting edge cavity 244 accommodates the cutting edge 80 for multiple blades 56. More specifically, a plurality of the cutting edge cavities 244 are disposed in equally spaced rows along the base 236 of the recess 232. A given cutting edge cavity 244 accommodates all of the blades 56 in a corresponding row on the wafer 130 (i.e., provides a space below the cutting edge 80 of each blade 56 in a given row on the wafer 130) in the illustrated embodiment. It should be appreciated that the base 236 of the recess 232 could be configured such that the cutting edge 80 of each individual blade 56 has its own individual cutting edge cavity 244 (not shown).

Multiple registrant cavities 256 are also formed on the base 236 of the recess 232 of the blade handle mounting fixture 224. Generally, these registrant cavities 256 are sized so that the registrants 32 on the bottom surface 48 of the blade handle 24 do not contact the fixture 224 while mounting a blade handle 24 on a particular cutting blade 56. Each registrant cavity 256 is defined by a base 260 that is vertically spaced from wafer supporting surface 238, and a side wall 264 that extends from the lower elevation base 260 to the higher elevation wafer supporting surface 238 (e.g., FIG. 18). In the illustrated embodiment, at least part of the side wall 264 of each registrant cavity 256 is disposed in perpendicular relation to the adjacent portion of the wafer supporting surface 238 of the base 236 of the recess 232. Any appropriate orientation of the side wall 264 of the various registrant cavities 256 may be utilized.

What is of principal importance in relation to each registrant cavity 256 is that they be sized and oriented on the upper surface 228 of the blade handle mounting fixture 224, such that each registration 84 of each blade 56 will be disposed over one of the registrant cavities 256 when the wafer 130 is disposed within the recess 232 on the fixture 224. More specifically, each registrant cavity 256 should be sized and oriented on the upper surface 228 of the fixture 224 such that a registrant cavity 256 is disposed below each registrant 32 of each blade handle 24 to keep the bottom wall 40 of each registrant 32 of each blade handle 24 in vertically spaced relation to the blade handle mounting fixture 224. In the illustrated embodiment, some registrant cavities 256 (those on an end of a row of registrant cavities 256) accommodate a single registrant 32 from a single blade handle 24, while other registrant cavities 256 accommodate a registrant 32 from a pair of blade handles 24 mounted on adjacently disposed blades 56 within a given row on the wafer 130. Although a plurality of rows of registrant cavities 256 could be utilized and spaced such that a given single registrant cavity 256 accommodated the registrant 32 of each blade handle 24 mounted on all of the blades 56 within a given row on the wafer 130 (not shown), the illustrated configuration is advantageous in relation to how the wafer 130 is supported by the fixture 224 for installation of the blade handles 24.

Figure 19:
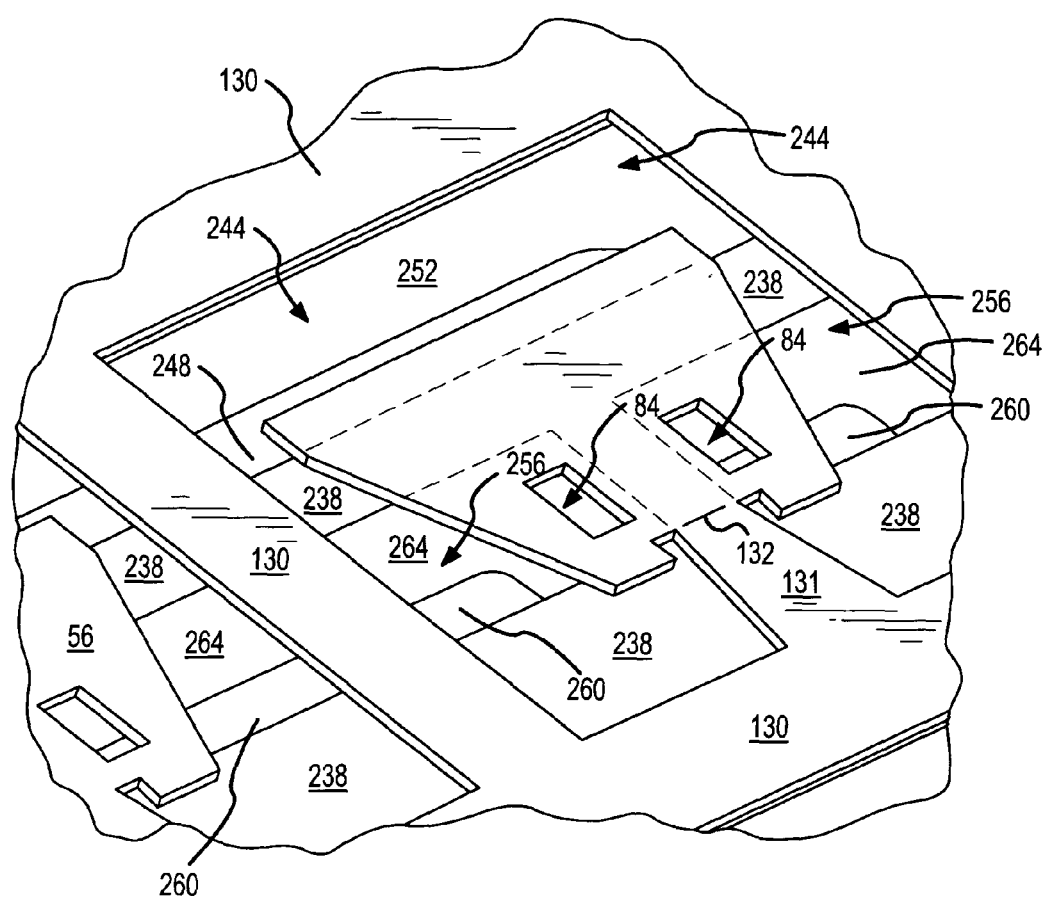
FIG. 19 is an enlarged, perspective view of a portion of the upper surface of the blade handle mounting fixture of FIG. 14 when supporting one of the cutting blades.

Appropriate support of the wafer 130 is provided by the illustrated configuration of the blade handle mounting fixture 224 when installing the blade handles 24 on the individual blades 56 that are still attached to and part of the wafer 130. Portions of the wafer supporting surface 238 that are disposed under, interface with, and support the representative blade 56 illustrated in FIG. 19, are shown by the dashed lines in FIG. 19. In this regard, each blade 56 of the wafer 130 is supported by the blade supporting surface 238 of the fixture 224 across the entire width of the blade 56 over a region that is spaced back from its cutting edge 80, which again is disposed over one of the cutting edge cavities 244 so as to be spaced from the fixture 224. Each blade 56 is also supported by the blade supporting surface 238 of the fixture 224 across the entire width of the blade 56 at or toward the rear of the blade 56 (e.g., proximate the rear surface 106). Finally, the blade 56 is also supported by the blade supporting surface 238 of the fixture 224 under its corresponding blade support tab 131 and along a longitudinally extending region between the registrant cavities 84. Therefore, the blades 56 do not tend to deflect downwardly a significant degree when installing blade handles 24 on the blades 56 at a time when these blades 56 are still attached to and part of the wafer 130. As noted above, preferably the blade 56 itself is directly supported by the fixture 224 (in one embodiment in coplanar relation with non-blade portions of the wafer 130), in a manner such that the net moment about the corresponding score 132 is zero (i.e., no torque) when mounting a blade handle 24 on the cutting blade 56.

Figure 14:
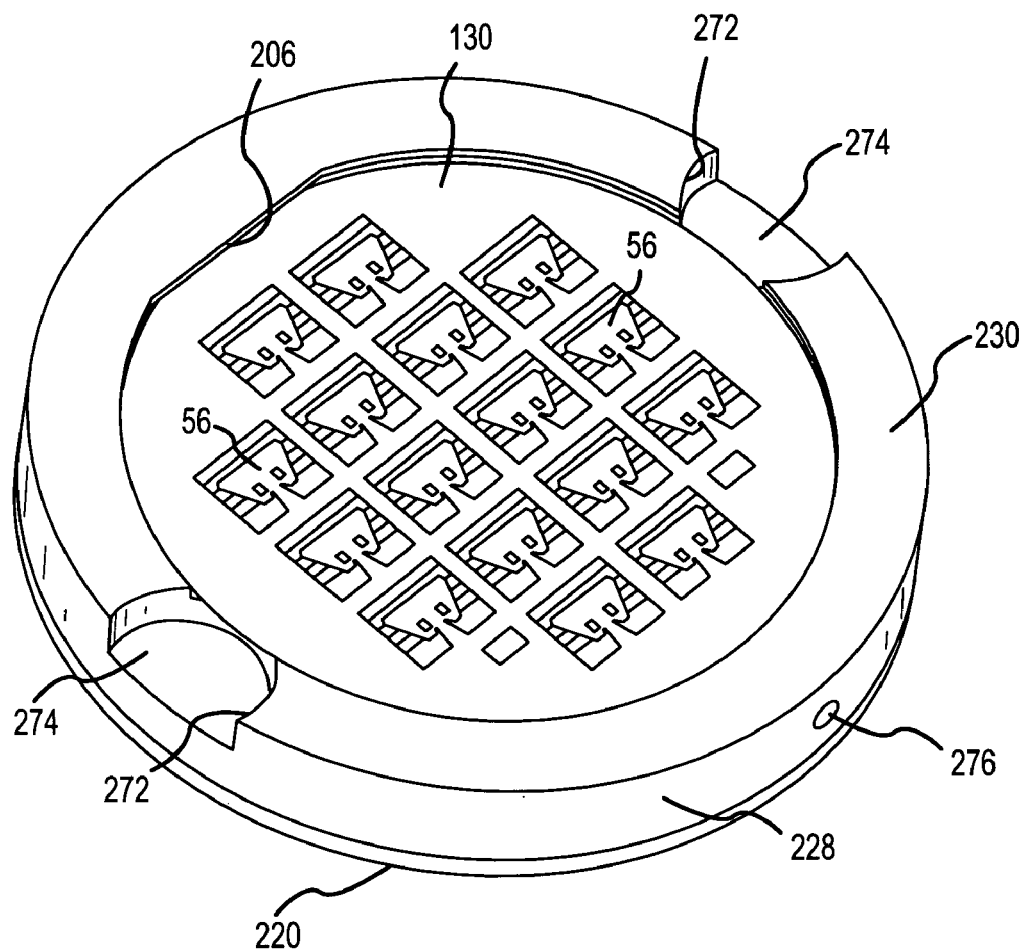
FIG. 14 is a perspective view of one embodiment of a fixture and base plate for installing blade handles on the cutting blades from the wafer of FIG. 12.
Figure 15:
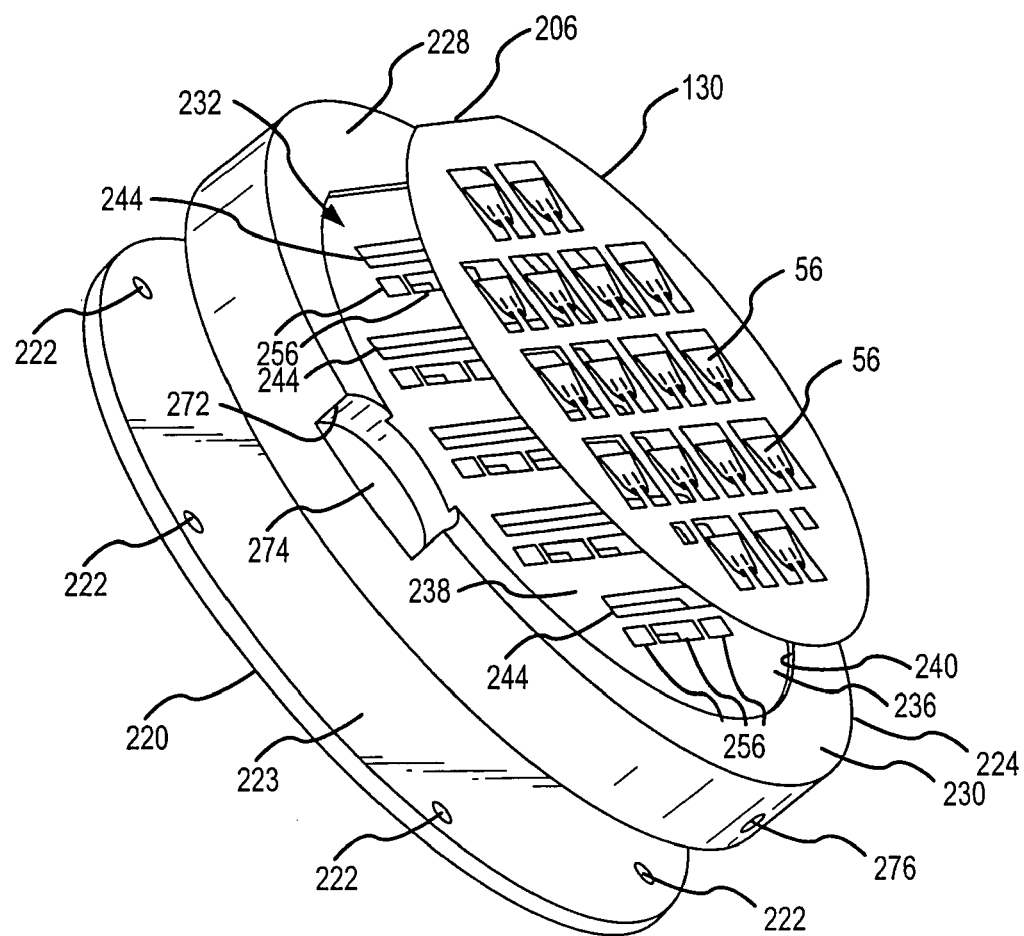
FIG. 15 is an exploded, perspective view of the blade handle mounting fixture and base plate of FIG. 14.

Summarizing the manner in which blade handles 24 are mounted on the blades 56, the wafer 130 with the blades 56 formed thereon is disposed within the recess 232 of the blade handle mounting fixture 224 in the manner illustrated in FIG. 14. A vacuum is drawn so as to retain portions of the wafer 130 against the wafer supporting surface 238 associated with the fixture 224. An appropriate adhesive may be applied on at least one of the top surface 60 of one or more of the cutting blades 56 and the bottom surface 48 of a corresponding number of blade handles 24. Each registrant 32 on the bottom surface 48 of a particular blade handle 24 is then disposed within a corresponding registration cavity 84 on a particular blade 56 by moving the blade handle 24 toward the fixture 224. Preferably, the registrants 32 of this blade handle 24 are initially disposed within the corresponding registration cavity 84 of the particular blade 24 so as to not contact its rear wall or registration surface 94. This may be utilized to seat the planar bottom surface 48 of the blade handle 24 on the planar top surface 60 of the cutting blade 56. The blade handle 24 may then be moved generally rearwardly until each registrant 32 cooperates with its corresponding registration surface 94, more typically a portion thereof. This then registers or aligns the cutting edge 80 of the particular cutting blade 56 relative to the microkeratome registration surface 28 of its corresponding blade handle 24, which in turn registers or aligns the cutting edge 80 of the cutting blade 56 in a desired position within the microkeratome 4. Once again, the microkeratome registration 28 of the blade handle 24 is registered or aligned relative to the cutting tool registration surface 14 of the head assembly 10 of the microkeratome 4.

Multiple cutting blades 56 may be formed on the wafer 130 prior to being positioned on the blade handle mounting fixture 224. A blade handle 24 may be mounted on each cutting blade 56 in the above-described manner. Blade handles 24 may be sequentially mounted on the various individual cutting blades 56, multiple blade handles 24 may be simultaneously mounted on multiple cutting blades 56, or blade handles 24 may be simultaneously mounted on all cutting blades 56 formed on the wafer 130. Regardless of how many cutting blades 56 are formed on the wafer 130 and the sequence of installing any blade handle(s) 24 thereon, the wafer 130 may be removed from the fixture 224 with a blade handle 24 being mounted on at least one cutting blade 56 and with the cutting blade(s) 56 remaining part of the wafer 130. That is, after a blade handle 24 has been mounted on at least one cutting blade 56, the wafer 130 may be removed from the fixture 224 and without having separated any such cutting blade 56 (with a blade handle 24 mounted thereon) from the wafer 130. Thereafter, the various individual cutting blades 56 with a blade handle 24 mounted thereon may be separated from the remainder of the wafer 130.

FIGS. 20–23 illustrate a desirable configuration for allowing blades 54 and their corresponding blade handles 24 to be separated from the wafer 130. Various characteristics of one configuration of a blade separation fixture 300 is disclosed by FIGS. 20–23. Initially, the wafer 130 is retained on the blade separation fixture 300 using a vacuum in the same manner discussed above in relation to the blade handle mounting fixture 224 of FIGS. 14–19. Therefore, the bottom surface of the blade separation fixture 300 will similarly include an annular groove and an annular seal ring of the type used by the blade handle mounting fixture 224, so that the base plate 220 may be attached to the fixture 300 in the same manner as the blade mounting fixture 224 to define a vacuum chamber. The blade separation fixture 300 will then also include a vacuum pull-down port, a vacuum linking port, and vacuum holes (not shown) of the type used by the blade mounting fixture 224 to draw a vacuum for retaining the wafer 130 on the fixture 300. Additional vacuum ports may be included on the upper surface 304 of the fixture 300 so as to retain the cutting tool 20 against the fixture 300 after its corresponding blade 56 has been separated from the remainder of the wafer 130 (e.g., by including vacuum ports on a blade interface wall 352 of the fixture 300).

An upper surface 304 of the blade separation fixture 300 is configured to suitably support the wafer 130 and maintain the same in a fixed position while separating blades 56 from the remainder of the wafer 130 using the blade handle 24 previously mounted thereon (e.g., in accordance with FIGS. 14–19). Generally, less than the entirety of the lower surface 138 of the wafer 130 is in actual contact with the upper surface 304 of the fixture 300. Moreover, the upper surface 304 of the fixture 300 is configured so as to reduce the potential for damage to the cutting edge 80 of each blade 56 while separating blades 56 from the remainder of the wafer 130. Finally, the upper surface 304 of the fixture 300 is configured so as to allow the bottom surface 48 of each blade handle 24 to remain properly seated on the top surface 60 of its corresponding blade 56 and in spaced relation to the fixture 300 (e.g., so as to be in interfacing relation, or at least in closely spaced and parallel relation).

The upper surface 304 of the blade separation fixture 300 includes a recess 312 having a base 320 that is vertically offset from an annular perimeter portion 308 of the upper surface 304. This base 320 includes a planar wafer supporting surface 324 (which includes a blade support tab section 326 for interfacing with and supporting each blade support tab 131 of the wafer 130, which again provides the interconnection between the blades 56 and the remainder of the wafer 130), a plurality of cutting edge cavities 328, and a plurality of registrant/pivot cavities 340. An annular side wall 316 of the recess 312 extends from the lower elevation wafer supporting surface 324 of the base 320 of the recess 312 to the higher elevation annular perimeter portion 308 of the upper surface 304 of the fixture 300. This annular side wall 316 at least substantially approximates a perimeter of the wafer 130. Preferably, the annular side wall 316 and the perimeter of the wafer 130 are disposed in closely spaced relation (e.g., such that there is no more than about a 1 millimeter gap between any portion of the annular side wall 316 and a corresponding portion of the perimeter of the wafer 130).

At least one notch 305 is formed on the upper surface 304 of the blade separation fixture 300. Each notch 305 has a base 306 that is vertically offset from the wafer supporting surface 324 of the base 320 of the recess 312. The base 305 of each notch 304 is disposed at a lower elevation than the wafer supporting surface 324 of the base 320 of the recess 312. There is a thereby a space between the wafer 130 and the base 306 of each notch 305. This space facilitates installation of the wafer 130 within the recess 312 of the blade separation fixture 300, as well as the removal of the wafer 130 from the blade separation fixture 300. Both manual (e.g., human operator) and a machine(s) are contemplated for one or both of the installation and removal of the wafer 130 relative to the blade separation fixture 300.

Multiple features are incorporated in the configuration of the base 320 of the recess 312 that is formed on the upper surface 304 of the blade separation fixture 300 for receipt of the wafer 130. One is that the various vacuum holes (not shown) intersect with the base 320 of the recess 312. Preferably these vacuum holes intersect with the wafer supporting surface 324 of the base 320 of the recess 312. The wafer supporting surface 324 interfaces with the lower surface 138 of the wafer 130 to vertically support the wafer 130 while on the fixture 300. When the wafer 130 is disposed within the recess 312, a vacuum is pulled against the lower surface 138 of the wafer 130 through the various vacuum holes, through the vacuum chamber, through the vacuum linking port, and through the vacuum pull-down port by an appropriate source and in the same manner discussed above in relation to the blade handle mounting fixture 224. Suction forces thereby retain the lower surface 138 of the wafer 130 against the planar wafer supporting surface 324 of the base 320 of the recess 312. Exactly how the suction or vacuum force is generated and transferred to the wafer 130 to retain the same against the fixture 300 is not of particular importance. Other configurations may be utilized to generate this type of retention force for the wafer 130 on the fixture 300.

Another feature of the base 320 of the recess 312 formed on the upper surface 304 of the blade separation fixture 300 is that it includes multiple cutting edge cavities 328. Each cutting edge cavity 328 is defined by a base 332 that is vertically spaced from the wafer supporting surface 324, and a side wall 336 that extends from the lower elevation base 332 to the higher elevation wafer supporting surface 328 (e.g., FIG. 22). In the illustrated embodiment, at least part of the side wall 336 of each cutting edge cavity 328 is disposed in perpendicular relation to the adjacent portion of the wafer supporting surface 324 of the base 320 of the recess 312. Any appropriate orientation of the side wall 336 of the various cutting edge cavities 328 may be utilized.

What is of principal importance in relation to each cutting edge cavity 328 is that they be sized and oriented on the upper surface 304 of the fixture 300 such that the cutting edge 80 of each blade 56 will be disposed over one of the cutting edge cavities 328 when the wafer 130 is disposed within the recess 312 on the fixture 300. That is, the cutting edge 80 of each blade 56 is disposed in vertically spaced relation to the blade separation fixture 300. In the illustrated embodiment, a given cutting edge cavity 328 accommodates the cutting edge 80 for multiple blades 56. More specifically, a plurality of the cutting edge cavities 328 are disposed in equally spaced rows along the base 320 of the recess 312. A given cutting edge cavity 328 accommodates all of the blades 56 in a corresponding row on the wafer 130 (i.e., provides a space below the cutting edge 80 of each blade 56 in a given row on the wafer 130) in the illustrated embodiment. It should be appreciated that the base 320 of the recess 312 could be configured such that the cutting edge 80 of each individual blade 56 had its own individual cutting edge cavity 328 (not shown).

Multiple registrant/pivot cavities 340 are also formed on the base 320 of the recess 312 of the blade separation fixture 300. Each registrant/pivot cavity 340 is defined by a base 344 that is vertically spaced from wafer supporting surface 324, a side wall 348 that extends from the lower elevation base 344 to the higher elevation wafer supporting surface 324 (e.g., FIG. 22), and a blade interface wall 352. In the illustrated embodiment, at least part of the side wall 348 of each registrant/pivot cavity 340 is disposed in perpendicular relation to the adjacent portion of the wafer supporting surface 324 of the base 320 of the recess 312. Any appropriate orientation of the side wall 348 of the various registrant/pivot cavities 340 may be utilized. The blade interface wall 352 defines the forward boundary of the corresponding registrant/pivot cavity 340 and is configured to interface with the bottom surface 64 of a blade 56 after being separated from the wafer 130 in a manner that will be discussed in more detail below.

What is of principal importance in relation to each registrant/pivot cavity 340 is that they be sized and oriented on the upper surface 304 of the fixture 300 such that each registration cavity 84 of each blade 56 will be disposed over one of the registrant/pivot cavities 340 when the wafer 130 is disposed within the recess 312 on the fixture 300. More specifically, each registrant/pivot cavity 340 should be sized and oriented on the upper surface 304 of the fixture 300 such that the registrant/pivot cavity 340 is disposed below each registrant 32 of each blade handle 24 to keep the bottom wall 40 of each registrant 32 of each blade handle 24 in vertically spaced to the blade separation fixture 300. In the illustrated embodiment, a given registrant/pivot cavity 340 accommodates the registrants 32 of multiple cutting tools 20. More specifically, a plurality of the registrant/pivot cavities 340 are disposed in equally spaced rows along the base 320 of the recess 312. A given registrant/pivot cavity 340 accommodates all of the blades 56 in a corresponding row on the wafer 130 (i.e., provides a space below the registrant cavities 84 of each blade 56 in a given row on the wafer 130) in the illustrated embodiment. It should be appreciated that the base 320 of the recess 312 could be configured such that each individual blade 56 had its own registrant/pivot cavity 340 (not shown).

The various blades 56 of the wafer 130 are suspended above the upper surface 304 of the blade separation fixture 300. That is, the blades 56 are disposed in vertically spaced relation to the underlying base 320 of the recess 312 of the blade separation fixture 300. Those portions of the wafer 130 that are disposed between the rows of blades 56, as well as the outer perimeter of the wafer 130 (e.g., the above-noted frame 128), interface with and are supported by the wafer supporting surface 324 of the fixture 300. Part of the wafer supporting surface 324, namely structures in the form of a plurality of blade supporting tab sections 326, interfaces with and supports the various blade support tabs 131 that interconnect each of the blades 56 with the remainder of the wafer 130. Each blade support tab section 326 extends toward, but not beyond, the score 132 of the corresponding blade support tab 131. Preferably, the distal end of each blade support tab section 326 is vertically aligned with a score 132.

A blade supporting surface 356 is located under the various blades 56 in a given row of the wafer 130 at a location that is longitudinally between the corresponding cutting edge cavity 328 and the corresponding registrant/pivot cavity 340. This blade supporting surface 356 is a planar surface, is parallel with the wafer supporting surface 324, and is recessed relative to the wafer supporting surface 324. That is, the blade supporting surface 356 is disposed at a lower elevation than the wafer supporting surface 324. Overlying blades 56 are thereby initially separated from the corresponding blade supporting surface 356 by a space when the wafer 130 is in the fixture 300. The above-noted blade interface wall 352 extends from the blade supporting surface 356 down to the base 344 of the corresponding registrant/pivot cavity 340. This blade interface wall 352 is a planar surface and is disposed at an angle a (FIG. 22) that is preferably within a range of about 15 degrees to about 30 degrees.

Figure 20:
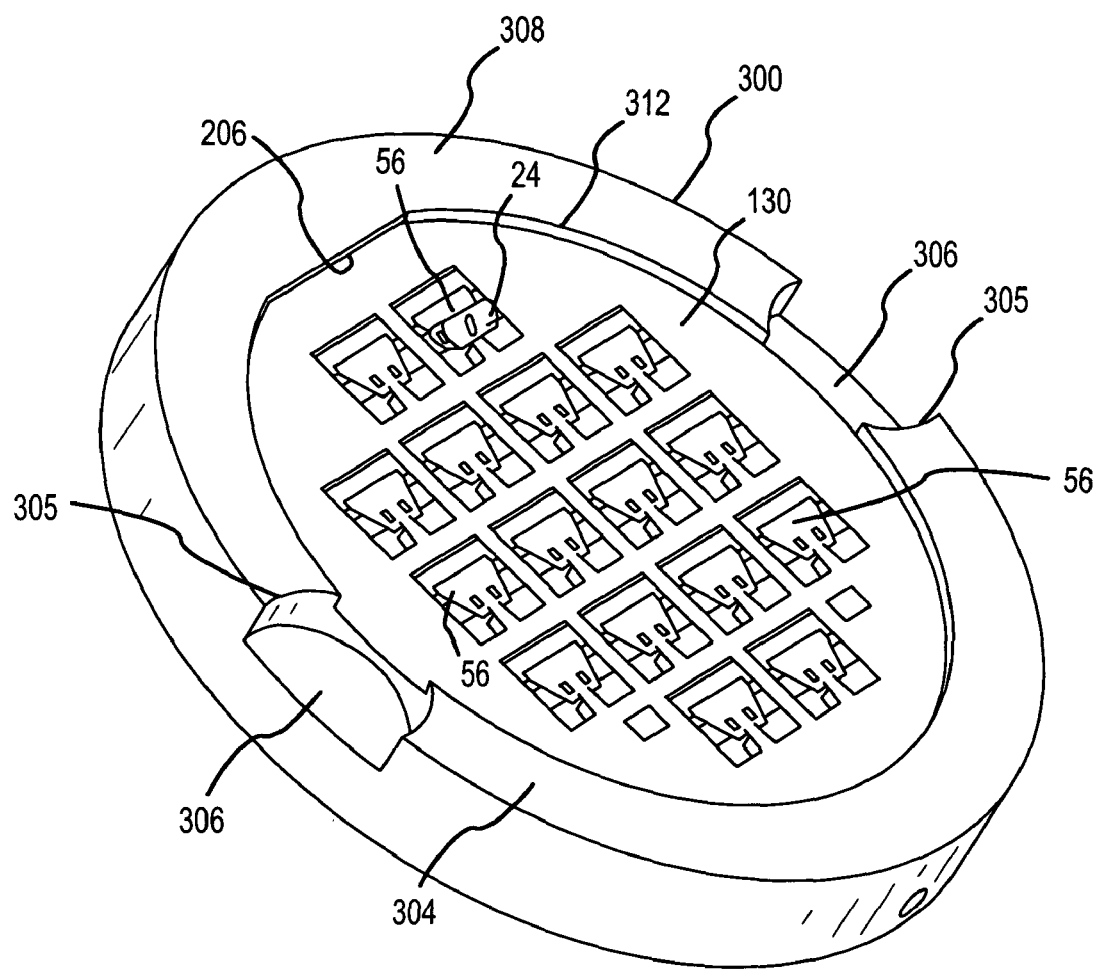
FIG. 20 is a perspective view of one embodiment of a blade separation fixture for separating blades from the wafer of FIG. 12.
Figure 21:
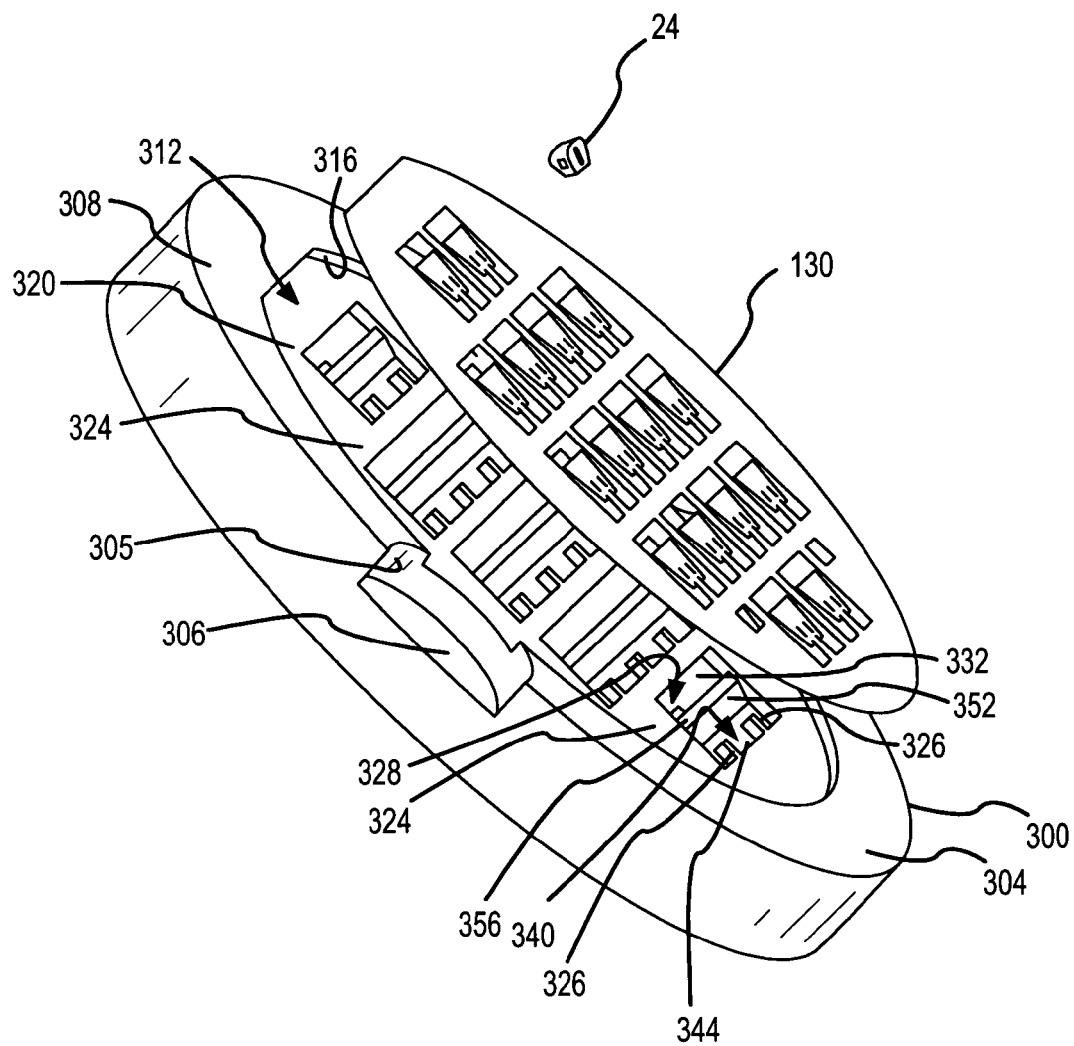
FIG. 21 is an exploded perspective view of the blade separation fixture of FIG. 20.
Figure 22:
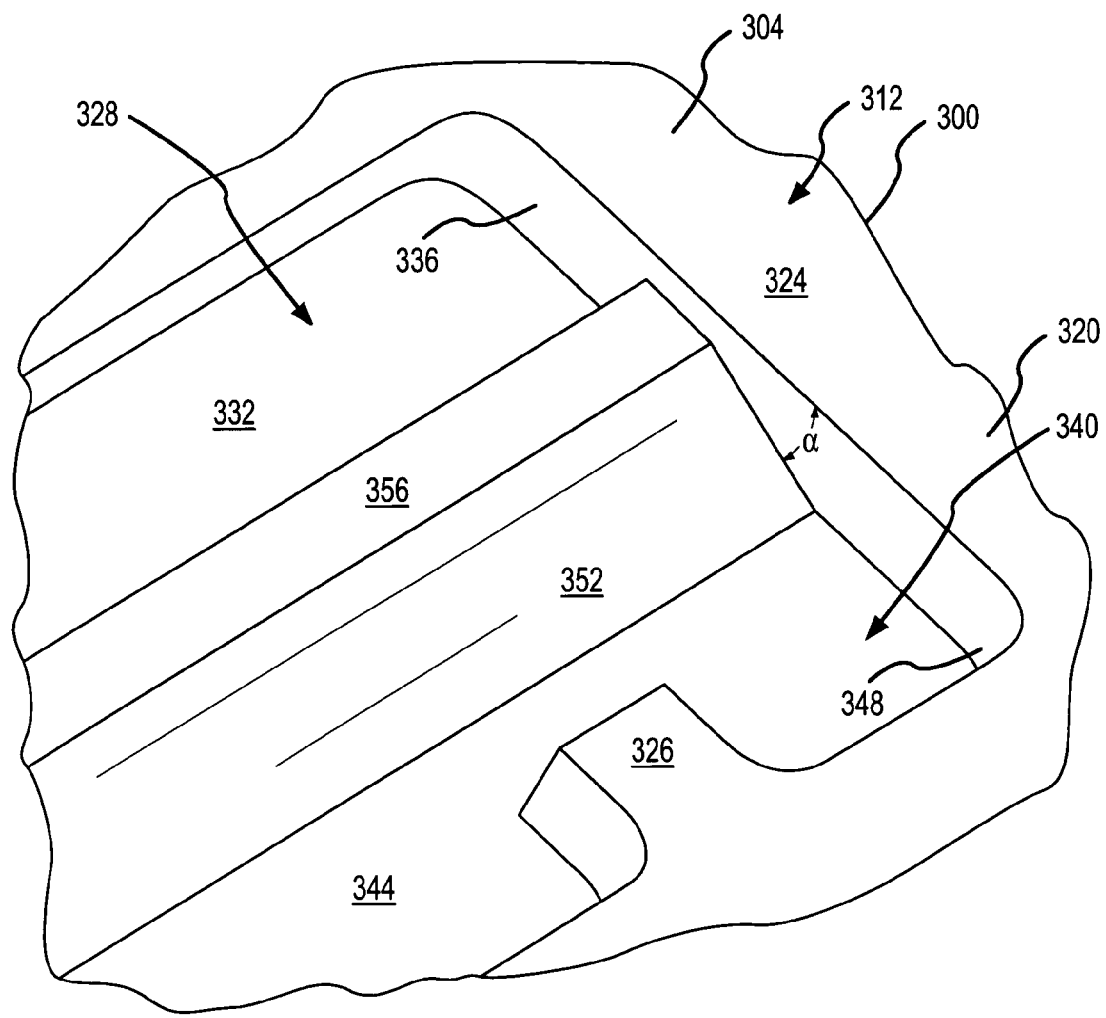
FIG. 22 is an enlarged perspective view of a portion of one of the cutting edge cavities and one of the registrant/pivot cavities used by the blade separation fixture of FIG. 20.
Figure 23:
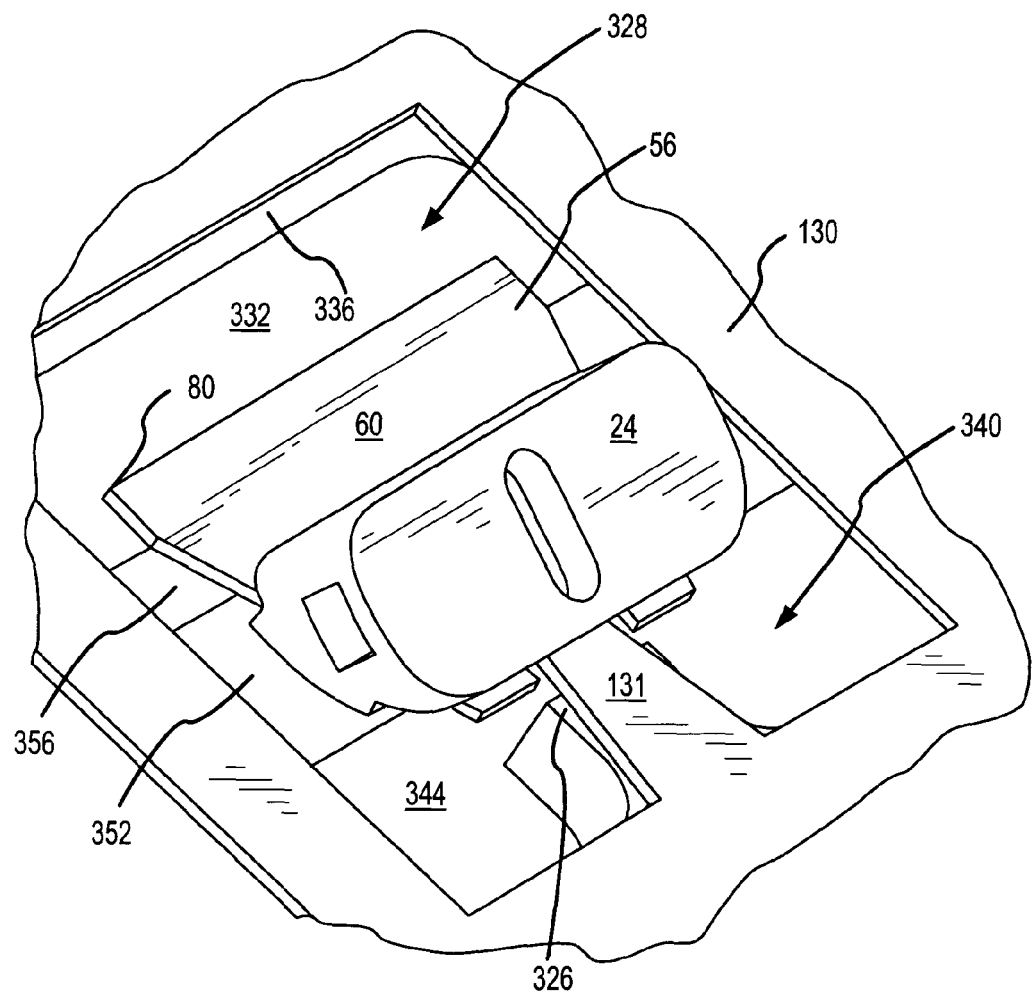
FIG. 23 is an enlarged perspective view of one of the cutting tools from the wafer of FIG. 12 being positioned over the cutting edge cavity and registrant/pivot cavity illustrated in FIG. 22.

Summarizing the manner in which blades 56 are separated from the remainder of the wafer 130, the wafer 130 is disposed within the recess 312 on the blade separation fixture 300 and in the manner illustrated in FIG. 20. Blade handles 24 typically will have been mounted to each of the blades 56 of the wafer 130 (utilizing the blade handle mounting fixture 224 discussed above in relation FIGS. 14–19) at this time, although any number of blades 56 may have a blade handle 224 mounted thereon and still utilize the blade separation fixture 300. A vacuum is drawn so as to retain portions of the wafer 130 (e.g., its frame 128) against the wafer supporting surface 324 associated with the fixture 300 by "pulling down" on portions of the wafer 130.

An at least generally downwardly directed force is then exerted on a particular blade handle 24 to separate its corresponding blade 56 from the wafer 130 in one embodiment. In another embodiment, this force is exerted directly on the blade 56. In either case, this may be done manually (e.g., by hand) or by a machine(s) (e.g., manually activated or in an automated manner). In one embodiment, this force is directed so as to be least generally perpendicular to the top surface 60 of the corresponding cutting blade 56. In any case, this type of force will cause the cutting blade 56 to deflect down toward the underlying blade supporting surface 356 a sufficient degree to cause the blade 56 (with its blade handle 24 mounted thereon) to separate from the remainder of the wafer 130 at least generally along its corresponding score 132. This separation preferably occurs before the blade 56 contacts the upper surface 304 of the fixture 300. The cutting edge 80 moves toward, but does not contact, the underlying fixture 300 during this deflection. One benefit of the configuration of the rear surface 106 of the cutting blade 56, namely by having the score 132 disposed within the notch 110 on the back surface 106 of the blade 56, is that even if the fracture does not occur exactly along the score 132, the wafer surface exposed by the fracture should still be longitudinally offset or spaced relative to the first sections 112 of the rear surface 106 of the blade 56.

Once the blade 56 has separated from the wafer 130 in the above-noted manner, the now separated blade 56 will continue in a downward direction until it contacts the underlying blade supporting surface 356. Since the force is being exerted on the blade 56 through its corresponding blade handle 24, the bottom surface 64 of the blade 56 will tend to move toward and most likely interface with an underlying blade interface wall 352. As noted above, suction forces or a vacuum may be used to retain the bottom surface 64 of each cutting blade 56 against an underlying blade interface wall 352 after being separated from the remainder of the wafer 130 in the above-noted manner. In any case, this of course moves its corresponding cutting edge 80 further away from the blade separation fixture 300 (e.g., by a pivoting or pivotal-like motion) so as to further reduce the potential for the cutting edge 80 being damaged during separation of the blade 56 from the wafer 130. A given cutting edge 80 thereby first moves at least generally toward the underlying fixture 300, and then at least generally away from the fixture 300.

The blade 56 again preferably moves into contact with the fixture 300 only after separating from the wafer 130. It initially does so by landing on the blade supporting surface 356 of the fixture 300. This blade supporting surface 356 is in effect a laterally extending beam about which the blade 56 pivots into contact with the inclined blade interface wall 352. Therefore, the cutting edge 80 first moves toward, but not to, the fixture 300 when the blade 56 is being separated from the wafer 130. When the cutting blade 56 does contact the fixture 300 after separation from the wafer 130 (the noted blade supporting surface 356), the cutting edge 80 of the blade 56 is still spaced from the fixture 300 by being over/within a cutting edge cavity 328. The blade 56 then pivots in a direction to move the cutting edge 80 away from the fixture 300, and in turn move its rear edge toward the fixture 300 (e.g., a teeter-totter-like action). The bottom surface 64 of the blade 56 will then interface with the inclined blade interface wall 352 such that the rear surface 106 of the blade 56 (or an associated edge) is disposed on the base 352 of the registrant/pivot cavity 340 (e.g., projecting at least generally downward) and further such that its cutting edge 80 is projecting at least generally upward and in spaced relation to the fixture 300. Therefore, the cutting edge 80 also preferably never contacts the fixture 300.

It is contemplated that each of the blades 56 may be sequentially removed from the remainder of the wafer 130 in the above-described manner (that is, one at a time), in one or more groups, or all simultaneously. In this regard, multiple cutting blades 56 may be formed on the wafer 130 prior to being positioned on the blade separation fixture 300. A blade handle 24 may be mounted on each cutting blade 56 as well before the wafer 130 is positioned on the fixture 300. Cutting blades 56 may be sequentially separated from the remainder of the wafer 130 in the above-noted manner, multiple cutting blades 56 may be simultaneously separated from the remainder of the wafer 130 in the above-noted manner, or all cutting blades 56 formed on the wafer 130 may be simultaneously separated from the remainder of the wafer 130 in the above-noted manner. Regardless of how many cutting blades 56 are formed on the wafer 130 and the sequence of separating cutting blades 56 from the remainder of the wafer 130, the wafer 130 may be removed from the fixture 300 after at least one cutting blade 56 has been separated from the remainder of the wafer 130. All cutting blades 56 are preferably separated from the wafer 130 prior to removing the wafer 130 from the fixture 300. However, any cutting blade 56 that has been separated from the remainder of the wafer 130 may be removed from the fixture 300 prior to or after the wafer 300 is removed from the fixture 300.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A method for making a cutting tool, comprising the steps of:
   executing a first positioning step comprising positioning a wafer on a first fixture, wherein said wafer comprises a first blade;
   mounting a first blade handle on said first blade while said wafer is on said first fixture;
   removing said wafer from said first fixture after said mounting step;
   executing a second positioning step comprising positioning said wafer on a second fixture;
   separating said first blade from a remainder of said wafer while said wafer is on said second fixture, wherein said separating step is executed after said mounting step.

2. A method, as claimed in claim 1, wherein:
   said first positioning step comprises positioning said wafer in a first recess formed on an upper surface of said first fixture, and wherein said second positioning step comprises positioning said wafer in a second recess formed on an upper surface of said second fixture.

3. A method, as claimed in claim 2, wherein:
   a perimeter of both said first and second recesses at least substantially approximates a perimeter of said wafer.

4. A method, as claimed in claim 1, wherein:
   said wafer comprises a lower surface, wherein each of said first and second positioning steps comprises disposing less than an entirety of said lower surface of said wafer in contact with said first and second fixtures, respectively.

5. A method, as claimed in claim 1, further comprising the step of:
   biasing said wafer toward said first fixture when said wafer is on said first fixture, and biasing said wafer toward said second fixture when said wafer is on said second fixture.

6. A method, as claimed in claim 5, wherein:
   each said biasing step comprises using a vacuum.

7. A method, as claimed in claim 1, further comprising the steps of:
   retaining said wafer on said first fixture using a vacuum, and retaining said wafer on said second fixture using a vacuum.

8. A method, as claimed in claim 1, further comprising the step of:
   maintaining a first cutting edge of said first blade in spaced relation to said first fixture.

9. A method, as claimed in claim 8, wherein:
   said maintaining step comprises disposing said first cutting edge of said first blade above a first cutting edge cavity formed on an upper surface of said first fixture.

10. A method, as claimed in claim 8, wherein:
    said maintaining step is executed throughout said mounting step.

11. A method, as claimed in claim 1, wherein:
    said wafer comprises a first score associated with said first blade, wherein said first positioning step comprises supporting said wafer with said first fixture directly under said first score, wherein said separating step utilizes said first score.

12. A method, as claimed in claim 11, further comprising the step of:
    aligning said first score with a predetermined crystal plane of said wafer.

13. A method, as claimed in claim 1, wherein:
    said wafer comprises a first score associated with said first blade, wherein said first positioning step comprises supporting said wafer such that said mounting step does not result in any net moment about said first score.

14. A method, as claimed in claim 1, wherein:
    said wafer comprises a first cantilever, wherein said first blade is disposed on an end of said first cantilever, wherein said first positioning step comprises supporting said first cantilever with said first fixture.

15. A method, as claimed in claim 14, wherein:
    said first positioning step comprises inhibiting any deflection of said first cantilever during said mounting step.

16. A method, as claimed in claim 1, wherein:
    said mounting step comprises maintaining said first blade handle in spaced relation with an entirety of said first fixture.

17. A method, as claimed in claim 1, wherein:
    said mounting step comprises applying an adhesive to at least one of said first blade handle and said first blade.

18. A method, as claimed in claim 17, wherein:
said adhesive is light curable, wherein said method further comprises disposing said first blade handle in a predetermined position relative to said first blade after said applying step, and thereafter exposing at least a portion of said adhesive to light to fix said first blade handle to said first blade.

19. A method, as claimed in claim 1, wherein:
said mounting step comprises disposing a first registrant extending from a lower surface of said first blade handle into a first registration cavity accessible through an upper surface of said first blade.

20. A method, as claimed in claim 19, wherein:
said disposing step comprises maintaining said first registrant in spaced relation with said first fixture.

21. A method, as claimed in claim 19, wherein:
said disposing step comprises directing said first registrant of said first blade handle toward a first registrant cavity formed on an upper surface of said first fixture that is aligned with said first registrant.

22. A method, as claimed in claim 1, wherein:
said mounting step comprises disposing first and second registrants extending from a lower surface of said first blade handle into first and second registration cavities accessible through an upper surface of said first blade.

23. A method, as claimed in claim 22, wherein:
said disposing step comprises supporting said first blade with said first fixture between said first and second registration cavities.

24. A method, as claimed in claim 1, wherein:
said mounting step comprises:
  disposing said first blade handle on an upper surface of said first blade;
  executing a first moving step comprising moving said first blade handle relative to said first blade after said disposing step; and
  terminating said first moving step upon registering said first blade handle to said first blade.

25. A method, as claimed in claim 24, wherein:
said disposing step comprises moving said first blade handle in a first direction toward said first blade, and wherein said first moving step comprises moving said blade handle in a second direction that is at least generally perpendicular to said first direction.

26. A method, as claimed in claim 24, wherein:
said first moving step comprises moving said first blade handle at least generally away from said first cutting edge of said first blade.

27. A method, as claimed in claim 24, wherein:
said first moving step comprises moving said first blade handle in a direction that is at least generally parallel to said upper surface of said first blade.

28. A method, as claimed in claim 24, wherein:
said registering step comprises a first registrant of said first blade handle engaging a first registration surface of said first blade.

29. A method, as claimed in claim 24, further comprising the step of:
securing said first blade handle to said first blade after said terminating step.

30. A method, as claimed in claim 1, wherein:
said wafer comprises a plurality of said first blades, wherein said method further comprises repeating said mounting step for each of said plurality of said first blades before said removing step.

31. A method, as claimed in claim 1, further comprising the step of:
maintaining a first cutting edge of said first blade in spaced relation to said second fixture.

32. A method, as claimed in claim 31, wherein:
said maintaining step comprises disposing said first cutting edge of said first blade above a first cutting edge cavity formed on an upper surface of said second fixture.

33. A method, as claimed in claim 31, further comprising the step of:
seating said first blade on said second fixture after said separating step, wherein said maintaining step is executed throughout an entirety of said separating step, from an end of said separating step to a start of said seating step, and throughout an entirety of said seating step.

34. A method, as claimed in claim 31, further comprising the step of:
executing a second maintaining step comprising maintaining said first cutting edge of said first blade in spaced relation to said first fixture.

35. A method, as claimed in claim 34, wherein:
said second maintaining step comprises disposing said first cutting edge of said first blade above a first cutting edge cavity formed on an upper surface of said first fixture.

36. A method, as claimed in claim 34, wherein:
said second maintaining step is executed throughout said mounting step, wherein said first cutting edge never contacts either said first fixture or said second fixture.

37. A method, as claimed in claim 1, further comprising the steps of:
maintaining a first cutting edge of said first blade in spaced relation to said first fixture throughout said mounting step; and
maintaining said first cutting edge of said first blade in spaced relation to said second fixture both throughout and after said separating step.

38. A method, as claimed in claim 1, further comprising the steps of:
seating said first blade on said second fixture after said separating step; and
maintaining a first cutting edge of said first blade in spaced relation to said second fixture throughout said separating step, from an end of said separating step to a start of said seating step, and throughout an entirety of said seating step.

39. A method, as claimed in claim 1, wherein:
said second positioning step comprises disposing an entirety of said first blade in spaced relation with said second fixture.

40. A method, as claimed in claim 1, wherein:
said second positioning step comprises suspending said first blade above said second fixture.

41. A method, as claimed in claim 40, wherein:
said wafer comprises a first cantilever, wherein said first blade is disposed on an end of said first cantilever, wherein said second positioning step comprises supporting at least a portion of said first cantilever with said second fixture.

42. A method, as claimed in claim 40, wherein:
said wafer further comprises a first blade support tab, wherein said first blade is disposed on an end of said first blade support tab, wherein said second positioning step comprises supporting at least a portion of said first blade support tab with said second fixture.

43. A method, as claimed in claim 1, wherein:
said separating step comprises fracturing said wafer.

44. A method, as claimed in claim 1, wherein:
said separating step is executed at least substantially along a line that is at least substantially parallel with said first cutting edge.

45. A method, as claimed in claim 1, wherein:
said wafer comprises a first score associated with said first blade, wherein said separating step comprises fracturing said wafer at least substantially along said first score.

46. A method, as claimed in claim 45, wherein:
said second positioning step comprises supporting said wafer proximate to said first score, while an entirety of said first blade is disposed in spaced relation to said second fixture.

47. A method, as claimed in claim 1, wherein:
said separating step comprises deflecting said first blade in a direction of said second fixture.

48. A method, as claimed in claim 1, wherein:
said separating step is executed with a first handle mounted on said first blade.

49. A method, as claimed in claim 48, wherein:
said separating step comprises applying a force on said first handle that is at least generally directed toward said first fixture.

50. A method, as claimed in claim 1, wherein:
said separating step comprises applying a force directly on said first blade that is at least generally directed toward said first fixture.

51. A method, as claimed in claim 1, wherein:
said separating step is completed before any portion of said first blade contacts said second fixture.

52. A method, as claimed in claim 1, wherein:
said separating step comprises executing a first moving step, wherein said method further comprises the step of executing a second moving step, wherein said first moving step comprises moving a first cutting edge of said first blade at least generally toward said second fixture without having said first cutting edge actually contact said second fixture, and wherein said second moving step comprises moving said first cutting edge of said first blade at least generally away from said second fixture before said first moving step causes said first cutting edge to contact said second fixture.

53. A method, as claimed in claim 1, further comprising the steps of:
moving said first blade into contact with said second fixture after said separating step, and then pivoting said first blade to direct a first cutting edge of said first blade at least generally away from said second fixture.

54. A method, as claimed in claim 1, further comprising the step of:
disposing a lower surface of said first blade against a first surface of said second fixture after said separating step such that a rear edge of said first blade is disposed at a lower elevation relative to a first cutting edge of said first blade, wherein said first surface is both inclined and planar.

55. A method, as claimed in claim 54, further comprising the step of:
retaining said first blade against said first surface.

56. A method, as claimed in claim 55, wherein:
said retaining step comprises using a vacuum.

57. A method, as claimed in claim 1, wherein:
said wafer comprises a plurality of said first blades, wherein said method further comprises repeating said separating step for each of said plurality of said first blades, and thereafter removing said wafer from said second fixture.

58. A method, as claimed in claim 1, wherein said wafer comprises a plurality of said first blades, wherein said method further comprises the steps of:
repeating said mounting step for each of said plurality of said first blades before said removing step;
repeating said separating step for each of said plurality of said first blades; and
removing said wafer from said second fixture after every said first blade has been separated from said wafer.

59. A method for making a cutting tool, comprising the steps of:
executing a first positioning step comprising positioning a wafer on a first fixture, wherein said wafer comprises a first blade;
maintaining a first cutting edge of said first blade in spaced relation to said first fixture, wherein said maintaining step comprises disposing said first cutting edge of said first blade above a first cutting edge cavity formed on an upper surface of said first fixture;
mounting a first blade handle on said first blade while said wafer is on said first fixture;
removing said wafer from said first fixture after said mounting step;
executing a second positioning step comprising positioning said wafer on a second fixture;
separating said first blade from a remainder of said wafer while said wafer is on said second fixture, wherein said separating step is executed after said mounting step.

60. A method for making a cutting tool, comprising the steps of:
executing a first positioning step comprising positioning a wafer on a first fixture, wherein said wafer comprises a first blade, wherein said wafer comprises a first score associated with said first blade, wherein said first positioning step comprises supporting said wafer such that said mounting step does not result in any net moment about said first score;
mounting a first blade handle on said first blade while said wafer is on said first fixture;
removing said wafer from said first fixture after said mounting step;
executing a second positioning step comprising positioning said wafer on a second fixture;
separating said first blade from a remainder of said wafer while said wafer is on said second fixture, wherein said separating step is executed after said mounting step.

61. A method for making a cutting tool, comprising the steps of:
executing a first positioning step comprising positioning a wafer on a first fixture, wherein said wafer comprises a first blade, wherein said wafer comprises a first cantilever, wherein said first blade is disposed on an end of said first cantilever, wherein said first positioning step comprises supporting said first cantilever with said first fixture, and wherein said first positioning step comprises inhibiting any deflection of said first cantilever during said mounting step;
mounting a first blade handle on said first blade while said wafer is on said first fixture;
removing said wafer from said first fixture after said mounting step;
executing a second positioning step comprising positioning said wafer on a second fixture;

separating said first blade from a remainder of said wafer while said wafer is on said second fixture, wherein said separating step is executed after said mounting step.

62. A method for making a cutting tool, comprising the steps of:
executing a first positioning step comprising positioning a wafer on a first fixture, wherein said wafer comprises a first blade;
mounting a first blade handle on said first blade while said wafer is on said first fixture, wherein said mounting step comprises disposing first and second registrants extending from a lower surface of said first blade handle into first and second registration cavities accessible through an upper surface of said first blade, and wherein said disposing step comprises supporting said first blade with said first fixture between said first and second registration cavities;
removing said wafer from said first fixture after said mounting step;
executing a second positioning step comprising positioning said wafer on a second fixture;
separating said first blade from a remainder of said wafer while said wafer is on said second fixture, wherein said separating step is executed after said mounting step.

63. A method for making a cutting tool, comprising the steps of:
executing a first positioning step comprising positioning a wafer on a first fixture, wherein said wafer comprises a first blade;
mounting a first blade handle on said first blade while said wafer is on said first fixture;
removing said wafer from said first fixture after said mounting step;
executing a second positioning step comprising positioning said wafer on a second fixture;
maintaining a first cutting edge of said first blade in spaced relation to said second fixture, wherein said maintaining step comprises disposing said first cutting edge of said first blade above a first cutting edge cavity formed on an upper surface of said second fixture;
separating said first blade from a remainder of said wafer while said wafer is on said second fixture, wherein said separating step is executed after said mounting step.

64. A method for making a cutting tool, comprising the steps of:
executing a first positioning step comprising positioning a wafer on a first fixture, wherein said wafer comprises a first blade;
mounting a first blade handle on said first blade while said wafer is on said first fixture;
removing said wafer from said first fixture after said mounting step;
executing a second positioning step comprising positioning said wafer on a second fixture;
maintaining a first cutting edge of said first blade in spaced relation to said second fixture;
separating said first blade from a remainder of said wafer while said wafer is on said second fixture, wherein said separating step is executed after said mounting step;
seating said first blade on said second fixture after said separating step, wherein said maintaining step is executed throughout an entirety of said separating step, from an end of said separating step to a start of said seating step, and throughout an entirety of said seating step.

65. A method for making a cutting tool, comprising the steps of:
executing a first positioning step comprising positioning a wafer on a first fixture, wherein said wafer comprises a first blade;
executing a first maintaining step comprising maintaining a first cutting edge of said first blade in spaced relation to said first fixture, wherein said first maintaining step comprises disposing said first cutting edge of said first blade above a first cutting edge cavity formed on an upper surface of said first fixture;
mounting a first blade handle on said first blade while said wafer is on said first fixture;
removing said wafer from said first fixture after said mounting step;
executing a second positioning step comprising positioning said wafer on a second fixture;
executing a second maintaining step comprising maintaining said first cutting edge of said first blade in spaced relation to said second fixture;
separating said first blade from a remainder of said wafer while said wafer is on said second fixture, wherein said separating step is executed after said mounting step.

66. A method for making a cutting tool, comprising the steps of:
executing a first positioning step comprising positioning a wafer on a first fixture, wherein said wafer comprises a first blade;
executing a first maintaining step comprising maintaining a first cutting edge of said first blade in spaced relation to said first fixture;
mounting a first blade handle on said first blade while said wafer is on said first fixture, wherein said first maintaining step is executed throughout said mounting step;
removing said wafer from said first fixture after said mounting step;
executing a second positioning step comprising positioning said wafer on a second fixture;
executing a second maintaining step comprising maintaining said first cutting edge of said first blade in spaced relation to said second fixture;
separating said first blade from a remainder of said wafer while said wafer is on said second fixture, wherein said separating step is executed after said mounting step, wherein said first cutting edge never contacts either said first fixture or said second fixture.

67. A method for making a cutting tool, comprising the steps of:
executing a first positioning step comprising positioning a wafer on a first fixture, wherein said wafer comprises a first blade;
mounting a first blade handle on said first blade while said wafer is on said first fixture;
removing said wafer from said first fixture after said mounting step;
executing a second positioning step comprising positioning said wafer on a second fixture;
separating said first blade from a remainder of said wafer while said wafer is on said second fixture, wherein said separating step is executed after said mounting step;
seating said first blade on said second fixture after said separating step; and
maintaining a first cutting edge of said first blade in spaced relation to said second fixture throughout said separating step, from an end of said separating step to a start of said seating step, and throughout an entirety of said seating step.

68. A method for making a cutting tool, comprising the steps of:

executing a first positioning step comprising positioning a wafer on a first fixture, wherein said wafer comprises a first blade;

mounting a first blade handle on said first blade while said wafer is on said first fixture;

removing said wafer from said first fixture after said mounting step;

executing a second positioning step comprising positioning said wafer on a second fixture, wherein said second positioning step comprises suspending said first blade above said second fixture, wherein said wafer comprises a first cantilever, wherein said first blade is disposed on an end of said first cantilever, wherein said second positioning step comprises supporting at least a portion of said first cantilever with said second fixture;

separating said first blade from a remainder of said wafer while said wafer is on said second fixture, wherein said separating step is executed after said mounting step.

69. A method for making a cutting tool, comprising the steps of:

executing a first positioning step comprising positioning a wafer on a first fixture, wherein said wafer comprises a first blade;

mounting a first blade handle on said first blade while said wafer is on said first fixture;

removing said wafer from said first fixture after said mounting step;

executing a second positioning step comprising positioning said wafer on a second fixture, wherein said second positioning step comprises suspending said first blade above said second fixture, wherein said wafer further comprises a first blade support tab, wherein said first blade is disposed on an end of said first blade support tab, wherein said second positioning step comprises supporting at least a portion of said first blade support tab with said second fixture;

separating said first blade from a remainder of said wafer while said wafer is on said second fixture, wherein said separating step is executed after said mounting step.

70. A method for making a cutting tool, comprising the steps of:

executing a first positioning step comprising positioning a wafer on a first fixture, wherein said wafer comprises a first blade;

mounting a first blade handle on said first blade while said wafer is on said first fixture;

removing said wafer from said first fixture after said mounting step;

executing a second positioning step comprising positioning said wafer on a second fixture; and separating said first blade from a remainder of said wafer while said wafer is on said second fixture, wherein said separating step is executed after said mounting step, wherein said wafer comprises a first score associated with said first blade, wherein said separating step comprises fracturing said wafer at least substantially along said first score, wherein said second positioning step comprises supporting said wafer proximate to said first score, while an entirety of said first blade is disposed in spaced relation to said second fixture.

71. A method for making a cutting tool, comprising the steps of:

executing a first positioning step comprising positioning a wafer on a first fixture, wherein said wafer comprises a first blade, that it turn comprises a first cutting edge, wherein said first positioning step comprises executing a first disposing step that in turn comprises disposing said first cutting edge of said first blade above a first cutting edge cavity formed on an upper surface of said first fixture;

mounting a first blade handle on said first blade while said wafer is on said first fixture;

removing said wafer from said first fixture after said mounting step;

executing a second positioning step comprising positioning said wafer on a second fixture, wherein said second positioning step comprises executing a second disposing step that in turn comprises disposing said first cutting edge of said first blade above a second cutting edge cavity formed on an upper surface of said second fixture;

separating said first blade from a remainder of said wafer while said wafer is on said second fixture, wherein said separating step is executed after said mounting step; and maintaining said first cutting edge of said first blade in spaced relation to each of said first and second fixtures while said wafer is positioned on said first and second fixtures, respectively, wherein said maintaining step comprises said first and second disposing steps.

72. A method, as claimed in claim 71, wherein:

said first positioning step further comprises engaging a first region of said wafer that is spaced from said first cutting edge of said first blade with said first fixture, wherein said engaging step keeps said wafer from deflecting toward said first fixture during said mounting step by an amount that would fracture said wafer in said first region;

said second positioning step further comprises executing a third disposing step that in turn comprises disposing said first region of said wafer above a first cavity formed on an upper surface of said second fixture; and said separating step comprises allowing said first region of said wafer to deflect toward said second fixture by said first region being disposed over said first cavity.

\* \* \* \* \*